(12) United States Patent
Levi et al.

(10) Patent No.: US 10,512,690 B2
(45) Date of Patent: Dec. 24, 2019

(54) COMPOSITE POLYDOTS AND APPLICATIONS THEREOF

(71) Applicant: Wake Forest University, Winston-Salem, NC (US)

(72) Inventors: Nicole Hope Levi, Winston-Salem, NC (US); Christopher Michael MacNeill, Fanwood, NJ (US); Elizabeth Grace Gurysh, Durham, NC (US); Louis Charles Argenta, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 256 days.

(21) Appl. No.: 15/303,171

(22) PCT Filed: Apr. 10, 2015

(86) PCT No.: PCT/US2015/025398
§ 371 (c)(1),
(2) Date: Oct. 10, 2016

(87) PCT Pub. No.: WO2015/157688
PCT Pub. Date: Oct. 15, 2015

(65) Prior Publication Data
US 2017/0028064 A1    Feb. 2, 2017

Related U.S. Application Data

(60) Provisional application No. 61/978,139, filed on Apr. 10, 2014.

(51) Int. Cl.
| | |
|---|---|
| *A61K 41/00* | (2006.01) |
| *C09K 11/06* | (2006.01) |
| *C08G 61/12* | (2006.01) |
| *A61K 9/00* | (2006.01) |
| *A61K 47/34* | (2017.01) |
| *A61K 9/51* | (2006.01) |
| *A61B 18/18* | (2006.01) |
| *A61N 5/06* | (2006.01) |
| *C09K 11/02* | (2006.01) |
| *A61K 47/68* | (2017.01) |
| *C08L 65/00* | (2006.01) |
| *B82Y 30/00* | (2011.01) |
| *A61B 18/00* | (2006.01) |

(52) U.S. Cl.
CPC .......... *A61K 41/0052* (2013.01); *A61B 18/18* (2013.01); *A61K 9/0009* (2013.01); *A61K 9/5146* (2013.01); *A61K 41/0057* (2013.01); *A61K 47/34* (2013.01); *A61K 47/6801* (2017.08); *A61N 5/062* (2013.01); *C08G 61/126* (2013.01); *C09K 11/025* (2013.01); *C09K 11/06* (2013.01); *A61B 2018/00577* (2013.01); *B82Y 30/00* (2013.01); *C08G 61/123* (2013.01); *C08G 61/124* (2013.01); *C08G 2261/124* (2013.01); *C08G 2261/1412* (2013.01); *C08G 2261/1424* (2013.01); *C08G 2261/18* (2013.01); *C08G 2261/3142* (2013.01); *C08G 2261/3223* (2013.01); *C08G 2261/3241* (2013.01); *C08G 2261/3243* (2013.01); *C08G 2261/3245* (2013.01); *C08G 2261/3246* (2013.01); *C08G 2261/3247* (2013.01); *C08G 2261/334* (2013.01); *C08G 2261/344* (2013.01); *C08G 2261/364* (2013.01); *C08G 2261/414* (2013.01); *C08G 2261/50* (2013.01); *C08G 2261/72* (2013.01); *C08G 2261/90* (2013.01); *C08G 2261/94* (2013.01); *C08G 2261/96* (2013.01); *C08L 65/00* (2013.01); *C08L 2201/54* (2013.01); *C08L 2203/02* (2013.01); *C08L 2205/02* (2013.01); *C09K 2211/1416* (2013.01); *C09K 2211/1458* (2013.01); *C09K 2211/1466* (2013.01); *C09K 2211/1483* (2013.01); *C09K 2211/1491* (2013.01)

(58) Field of Classification Search
CPC ...................................................... C09K 11/06
See application file for complete search history.

(56) References Cited

U.S. PATENT DOCUMENTS

| 2013/0011864 A1 | 1/2013 | Wang et al. | |
|---|---|---|---|
| 2013/0234068 A1 | 9/2013 | Chiu et al. | |
| 2015/0069302 A1* | 3/2015 | Levi ....................... | A61K 47/59 252/500 |

FOREIGN PATENT DOCUMENTS

| CN | 103480006 A | 1/2014 |
|---|---|---|
| WO | 20130155463 A1 | 10/2013 |

OTHER PUBLICATIONS

Ding et al., Small, 2013, 9, 18, abstract, 1 page.*
International Search Report and Written Opinion issued in corresponding International Application No. PCT/US2015/025398 dated Jul. 15, 2015, 8 pages.

* cited by examiner

*Primary Examiner* — Kyle A Purdy
(74) *Attorney, Agent, or Firm* — J. Clinton Wimbish; Nexsen Pruet PLLC

(57) ABSTRACT

The present invention relates to nanoparticle compositions and, in particular, to composite polymeric nanoparticle compositions. A composite nanoparticle described herein comprises a photoluminescent polymeric component and a photo-thermal polymeric component. The photoluminescent polymeric component and the photo-thermal polymeric component can each comprise a single polymeric species or multiple polymeric species.

38 Claims, 25 Drawing Sheets

D   is an electron donor group made up of either C=C, alkynyl, aryl or heteroaryl containing 1-20 rings and may be substituted by one or more R groups. D may have one of the following structures:

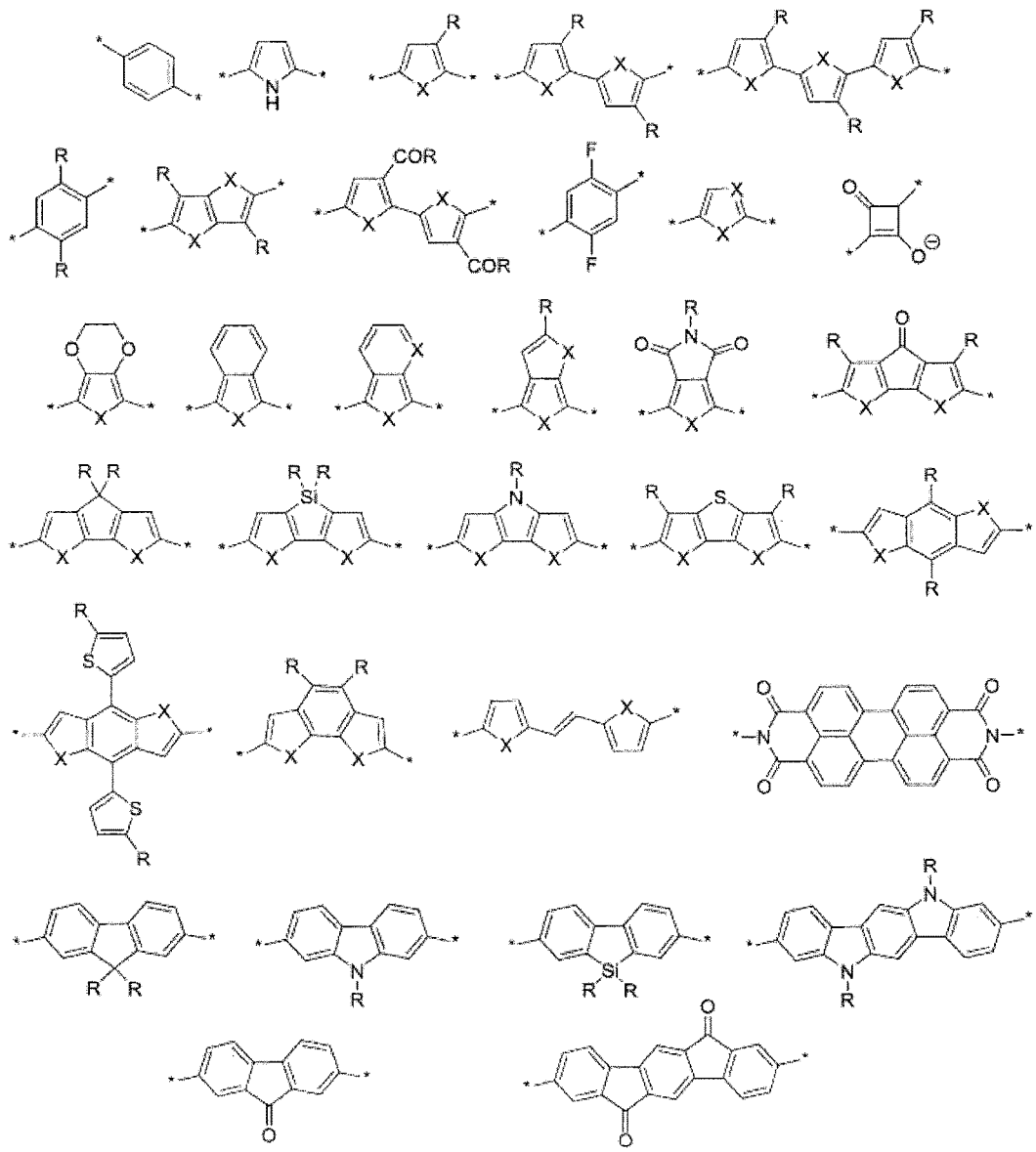

R or R1   denotes a H, Br, Cl, I, F, NO2, CN, NCS, NH2, CF3, polyethylene glycol (PEG), carboxy, azido or amine terminated PEG, COR2, COOR2, COOH, CONHR2, CONR2R3, NR2R3R4, straight chain, branched, substituted or unsubstituted alkyl groups from 1-40 carbon atoms potentially consisting of one or more adjacent heteroatom substitutions and potentially consisting of one or more substituent R2 groups, aryl, heteroaryl, aryloxy, heteroaryloxy, O-aryl, O-heteroaryl, N-alkyl, N-aryl R2, R3 or R4   denotes H or alkyl groups from 1-40 carbon atoms, aryl groups X   denotes O, NH, CH2, C-RR1, N-R, S, Se, Te

FIGURE 1

A, A1, A2, A3 are electron acceptor groups that are independent of one another. They can be C=C, alkynyl, aryl, heteroaryl with 1-20 rings and may be substituted by one or more R groups or one or more A groups. A, A1, A2 and A3 may have one of the following structures:

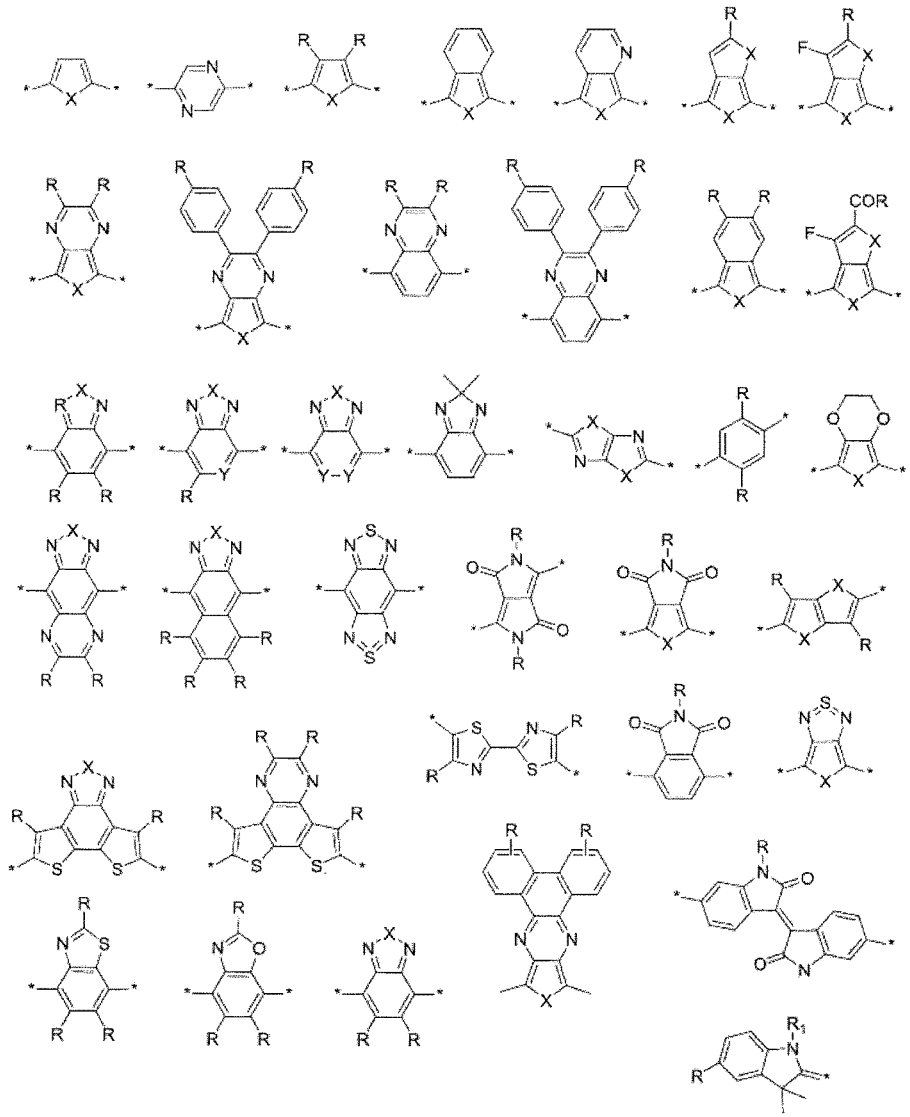

R or R1 denotes a H, Br, Cl, I, F, NO2, CN, NCS, NH2, CF3, polyethylene glycol (PEG), carboxy, azido or amine terminated PEG, COR2, COOR2, COOH, CONHR2, CONR2R3, NR2R3R4, straight chain, branched, substituted or unsubstituted alkyl groups from 1-40 carbon atoms potentially consisting of one or more adjacent heteroatom substitutions and potentially consisting of one or more substituent R2 groups, aryl, heteroaryl, aryloxy, heteroaryloxy, O-aryl, O-heteroaryl, N-alkyl, N-aryl R2, R3 or R4 denotes H or alkyl groups from 1-40 carbon atoms, aryl groups X denotes O, NH, CH2, C-RR1, N-R, S, Se, Te

FIGURE 2

COMPOSITE POLYDOTS AND APPLICATIONS THEREOF

RELATED APPLICATION DATA

This application is a National Phase of PCT/US2015/025398, filed Apr. 10, 2015, which claims priority pursuant to 35 U.S.C. § 119(e) to U.S. Provisional Patent Application Ser. No. 61/978,139 filed Apr. 10, 2014, each of which are incorporated herein by reference in their entireties.

FIELD

The present invention relates to nanoparticle compositions and, in particular, to composite polymeric nanoparticle compositions.

BACKGROUND

Electrically conductive conjugated polymers show excellent charge transport properties making them desirable materials for nanostructured compositions. Many conjugated polymers have been fabricated into devices such as organic photovoltaics, light emitting diodes and field-effect transistors. The low band gap electronic structure of some conjugated polymers permits such polymers to be efficient electron donors due to enhanced absorption of visible and near-infrared light for exciton generation and subsequent transfer of charge to an electron acceptor, such as a $C_{60}$ derivative.

Conjugated polymers are readily soluble in organic solvents and concomitantly insoluble in aqueous media. Such insolubility has limited application of conjugated polymer systems to a variety of applications requiring compatibility with aqueous solvents and/or phases, such as biological applications.

SUMMARY

In one aspect, composite nanoparticle compositions and systems are described herein demonstrating compatibility with aqueous and aqueous-based media. The ability to provide aqueous compatible nanoparticle compositions from previously water insoluble conjugated polymeric systems, in some embodiments, can facilitate use of such systems in a variety of aqueous applications, including biological applications.

A composite nanoparticle described herein comprises a photoluminescent polymeric component and a photo-thermal polymeric component. The photoluminescent polymeric component and the photo-thermal polymeric component can each comprise a single polymeric species or multiple polymeric species. In some embodiments, for example, the photoluminescent polymeric component comprises a polymeric species having a wider bandgap and lower molecular weight than the polymeric species of the photo-thermal polymeric component. Further, the composite nanoparticle can have different architectures. In some embodiments, the photoluminescent polymeric component and the photo-thermal polymeric component are dispersed throughout the composite nanoparticle. In other embodiments, the photoluminescent polymeric component and the photo-thermal polymeric component are localized to different regions of the composite nanoparticle. For example, the photo-thermal polymeric component can be localized to the core of composite nanoparticle and the photoluminescent component localized to surface or exterior regions of the composite nanoparticle. Additionally, composite nanoparticles described herein, in some embodiments, exhibit a hollow structure including hollow spheres and hollow rods. The photoluminescent polymeric component and photo-thermal polymeric component, for example, can form a shell defining a cavity.

The ratio of photo-thermal polymeric component to photoluminescent polymeric component can be varied depending on the desired properties of the composite nanoparticle. The photo-thermal component can be increased or decreased depending on desired amount of heat generation from the nanoparticle. Similarly, the photoluminescent polymeric component can be increased or decreased depending on the desired intensity of photoluminescence from the nanoparticle.

A composite nanoparticle, in another embodiment, comprises a nanoparticle support and a polymeric coating over the nanoparticle support, the polymeric coating comprising photoluminescent polymeric phase and a photo-thermal polymeric phase. A nanoparticle support can comprise carbon nanoparticles, including single-walled carbon nanotubes, multi-walled carbon nanotubes, fullerenes or graphene or combinations thereof. Alternatively, a nanoparticle support can comprise inorganic nanoparticles, such as metal nanoparticles, metal oxide nanoparticles such as silica, semiconductor nanoparticles, quantum dots or combinations thereof. In some embodiments, a nanoparticle support comprises other organic nanoparticles including biopolymer nanoparticles, cellulose and cellulose derivative nanoparticles, nanoparticles of non-electrically conductive polymers or combinations thereof. Further a nanoparticle support can have any desired shape. The nanoparticle support, for example, can have an isotropic shape or anisotropic shape.

In another aspect, compositions comprising composite nanoparticles are described herein. A composition, in some embodiments, comprises an aqueous or aqueous-based medium and composite nanoparticles disposed in the aqueous or aqueous-based medium, the composite nanoparticles comprising a photoluminescent polymeric component and a photo-thermal polymeric component. The composite nanoparticles, in some embodiments, are dispersed throughout the aqueous or aqueous-based medium. Alternatively, the composite nanoparticles are solubilized in the aqueous or aqueous-based medium.

Additional compositions incorporating composite nanoparticles described herein include wound dressings. A wound dressing comprises a support phase and composite nanoparticles in contact with the support phase, the composite nanoparticles comprising a photoluminescent polymeric component and a photo-thermal polymeric component. The support phase can be formed of traditional wound dressing materials including elastomeric materials, such as biodegradable and/or non-biodegradable elastomeric materials.

In another aspect, tissue treatment systems are described herein. A tissue treatment system comprises a source of radiation and a composition including an aqueous or aqueous-based medium and composite nanoparticles disposed in the aqueous or aqueous-based medium, the composite nanoparticles comprising a photoluminescent polymeric component and a photo-thermal polymeric component, wherein radiation emitted by the radiation source at least partially falls within the absorption profile of the photoluminescent polymeric component, photo-thermal polymeric component or both. Alternatively, wound dressings described herein can be employed in conjunction with a radiation source to provide a tissue treatment system.

In addition to compositions, methods of making composite nanoparticles are described herein. A method of making composite nanoparticles comprises providing a mixture including a photoluminescent polymeric component and photo-thermal polymeric component in a liquid medium and sonicating the mixture to form the composite nanoparticles comprising the photoluminescent component associated with the photo-thermal polymeric component. In some embodiments, the photoluminescent polymeric component and the photo-thermal polymeric component are present throughout the composite nanoparticle. Alternatively, a method of making composite nanoparticles comprises providing a mixture including a photo-thermal polymeric component in a liquid medium and sonicating the mixture to form photo-thermal polymeric nanoparticles. A photoluminescent polymeric component is added to the mixture comprising the photo-thermal polymeric nanoparticles and the resulting mixture is sonicated to at least partially coat the photo-thermal polymeric nanoparticles with the photoluminescent polymeric component. In such embodiments, the composite nanoparticles can have a core-shell architecture.

In another embodiment, a method of making composite nanoparticles comprises providing a mixture including a photoluminescent polymeric component in a liquid medium and sonicating the mixture to form photoluminescent polymeric nanoparticles. A photo-thermal polymeric component is added to the mixture comprising the photoluminescent polymeric nanoparticles and the resulting mixture is sonicated to at least partially coat the photoluminescent polymeric nanoparticles with the photo-thermal polymeric component. In such embodiments, the composite nanoparticles can have a core-shell architecture.

In a further aspect, methods of treating tissue are described herein. A method of treating tissue comprises providing a composition including an aqueous or aqueous-based medium and composite nanoparticles in the aqueous or aqueous-based medium, the nanoparticles comprising a photoluminescent polymeric component and a photo-thermal polymeric component. The composition is positioned in the tissue, and the tissue is heated by irradiating the composition with radiation at least partially falling within the absorption profile of the photo-thermal polymeric component. In some embodiments, the method further comprises determining the position of the composition by irradiating the composition with radiation at least partially falling within the absorption profile of the photoluminescent polymeric component.

Importantly, the photo-thermal polymeric component and/or photoluminescent polymeric component of compositions and methods described herein can be substituted by a photo-thermal oligomeric component and/or photoluminescent oligomeric component. Similarly, the photo-thermal polymeric component and/or photoluminescent polymeric component of compositions and methods described herein can be also substituted by a photo-thermal small molecule component and/or photoluminescent small molecule component.

These and other embodiments are described in greater detail in the detailed description which follows.

BRIEF DESCRIPTION OF THE DRAWINGS

FIG. 1 illustrates monomeric species of a water insoluble conjugated polymer according to some embodiments described herein.

FIG. 2 illustrates monomeric species of a water insoluble conjugated polymer according to some embodiments described herein.

DETAILED DESCRIPTION

Figure 3:
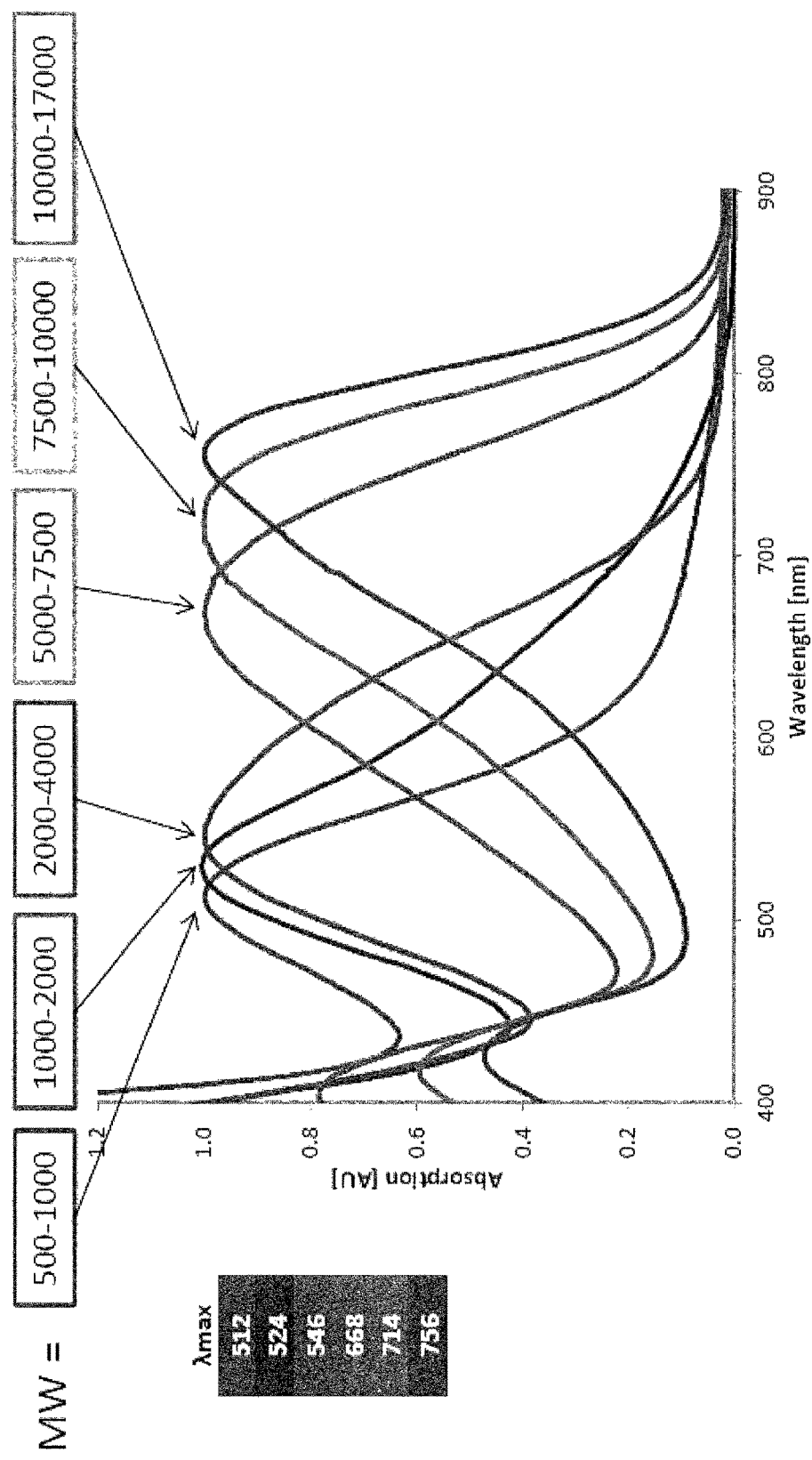
FIG. 3 illustrates absorption spectra red-shifting of PCP-DTBSe with increasing number average molecular weight according to one embodiment described herein.

Embodiments described herein can be understood more readily by reference to the following detailed description and examples and their previous and following descriptions. Elements, apparatus and methods described herein, however, are not limited to the specific embodiments present in the detailed description and examples. It should be recognized that these embodiments are merely illustrative of principles of the present invention. Numerous modifications and adaptations will be readily apparent to those of skill in the art without departing from the spirit and scope of the invention.

I. Composite Nanoparticles

A composite nanoparticle described herein comprises a photoluminescent polymeric component and a photo-thermal polymeric component. The photoluminescent polymeric component and the photo-thermal polymeric component can each comprise a single polymeric species or multiple polymeric species. In some embodiments, for example, the photoluminescent polymeric component comprises a polymeric species having a wider bandgap and lower molecular weight than the polymeric species of the photo-thermal polymeric component. Further, the composite nanoparticle can have different architectures. In some embodiments, the photoluminescent polymeric component and the photo-thermal polymeric component are dispersed throughout the composite nanoparticle. In other embodiments, the photoluminescent polymeric component and the photo-thermal polymeric component are localized to different regions of the composite nanoparticle. For example, the photo-thermal polymeric component can be localized to the core of composite nanoparticle and the photoluminescent component localized to surface or exterior regions of the composite nanoparticle. Additionally, composite nanoparticles described herein, in some embodiments, exhibit a hollow structure including hollow spheres and hollow rods. The photoluminescent polymeric component and photo-thermal polymeric component, for example, can form a shell defining a cavity.

The ratio of photo-thermal polymeric component to photoluminescent polymeric component can be varied depending on the desired properties of the composite nanoparticle. The photo-thermal component can be increased or decreased depending on desired amount of heat generation from the nanoparticle. Similarly, the photoluminescent polymeric component can be increased or decreased depending on the desired intensity of photoluminescence from the nanoparticle.

A. Photo-thermal Polymeric Component

Turning now to specific components, composite nanoparticles described herein comprise a photo-thermal polymeric component. A photo-thermal polymeric component is operable to provide thermal energy to the environment surrounding the composite nanoparticle when irradiated with radiation falling within the absorption profile of the photo-thermal polymeric component. As described herein, the photo-thermal polymeric component can comprise one or more polymeric species. Polymeric species of the photo-thermal component, in some embodiments, are conjugated polymeric species. Various conjugated polymeric species exhibiting a thermal response to radiation may be employed in the photo-thermal polymeric component. For example, conjugated polymeric species having a bandgap ranging from about 1.1 eV to about 1.8 eV can be used in the photo-thermal polymeric component. Bandgap and associated radiation absorption profile of the photo-thermal polymeric component can be tailored to spectral requirement(s) of a particular application. As discussed further herein, a photo-thermal component having an absorption profile in the near infrared region (NIR) can be used for tissue treatment applications where radiation is required to penetrate tissue to reach the composite nanoparticles. For example, polymeric species of the photo-thermal component can have an absorption profile of 700 nm to 1000 nm. Further, the spectral response of the photo-thermal polymeric component can be broadened or narrowed by the use of multiple polymeric species or a single polymeric species respectively.

Any thermally responsive conjugated polymer not inconsistent with the objectives of the present invention can be used in the photo-thermal polymeric component. In some embodiments, the conjugated polymer is a homopolymer. For example, a homopolymer can be constructed of a donor monomeric species (D), wherein D is a monocyclic, bicyclic or polycyclic arylene or monocyclic, bicyclic or polycyclic heteroarylene. The arylene structures, in some embodiments, can be fused or linked. A water insoluble conjugated homopolymer, in some embodiments, is constructed of a monomer selected from the group consisting of aniline, pyrrole, thiophene, 3-substituted thiophene, bithiophene, terthiophene, selenophene, 3-substituted selenophene, isothianaphthene, p-phenylenevinylene, ethylenedioxythiophene, propylenedioxythiophene, 2,7-fluorene, substituted 2,7-fluorene, 2,7-carbazole, substituted 2,7-carbazole, thieno[3,2-b]thiophene, thieno[3,4-b]thiophene, dithienothiophene, cyclopenta[2,1-b:3,4-b]dithiophene, substituted cyclopenta[2,1-b:3,4-b']dithiophene, dithieno[3,2-b:2',3'-d]silole, benzo[1,2-b:4,5-b']dithiophene, benzo[1,2-b;3,4-b'] dithiophene, indolo[3,2-b]carbazoles, dithieno[3,2-b:2',3'-d]pyrrole, diketopyrrolopyrrole, pentacene, heptacene and perylenediimine. Some suitable donor monomeric species are further illustrated in FIG. 1. In the structures of FIG. 1, X can be O, N, S or Se. In some embodiments comprising more than one X, each X can independently be O, N, S, Se or Te. In addition, R, $R_1$, $R_2$ and $R_3$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms.

Additionally, a conjugated homopolymer of the photo-thermal polymeric component can be constructed of an acceptor monomeric species (A, $A_1$, $A_2$, $A_3$ in formula herein), wherein the acceptor monomeric species is a monocyclic, bicyclic or polycyclic arylene or monocyclic, bicyclic or polycyclic heteroarylene. The arylene structures, in some embodiments, can be fused or linked. A water insoluble conjugated homopolymer, in some embodiments, is constructed of a monomer selected from the group consisting of pyrrole, aniline, thiophene, ethlyenedioxythiophene, p-phenylenevinylene, benzothiadiazole, pydridinethiadazole, pyridineselenadiazole, benzoxadiazole, benzoselenadiazole, thieno[3,4-b]pyrazine, thieno[3,4-b]thiophene, thieno[3,2-b]thiophene, [1,2,5]thiadiazolo[3,4-g]quinoxaline, pyrazino[2,3-g]quinoxaline, thienopyrrolidinone and isothianaphthene. Some suitable acceptor monomeric species (A, $A_1$, $A_2$, $A_3$) are further illustrated in FIG. 2. In the structures of FIG. 2, X can be O, N, S, Se or Te. In some embodiments comprising more than one X, each X can independently be O, N, S or Se. In addition, R, $R^1$ and $R^2$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms. In some embodiments, an acceptor monomeric species is a diketopyrrolopyrrole. For example, a diketopyrrolopyrrole is of the formula;

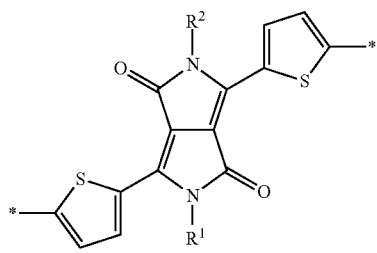

wherein $R^1$ and $R^2$ are defined above.

Alternatively, in some embodiments, a conjugated polymer of the photo-thermal component is a copolymer of two or more repeating units. For example, a water insoluble conjugated polymer can be constructed of two or more monomeric species selected from the group consisting of D and A monomeric species described herein. In some embodiments, conjugated polymer is a copolymer of a donor-acceptor (D-A) architecture. For example, a D-A water insoluble conjugated polymer can be composed of cyclopentadithiophene and 2,1,3-benzothiadiazole (PCPDTBT) or cyclopentadithiophene and 2,1,3-benzoselenadiazole (PCPDTBSe). In some embodiments, a water insoluble conjugated polymer has the structure of Formula (I):

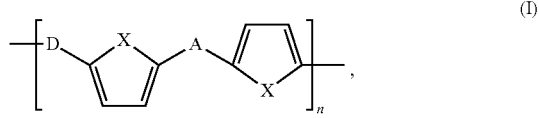

wherein D is a donor monomeric species described herein, A is an acceptor monomeric species described herein, and each X is independently O, N, S or Se. In some embodiments, a D-A conjugated polymer of the photo-thermal component is of formula:

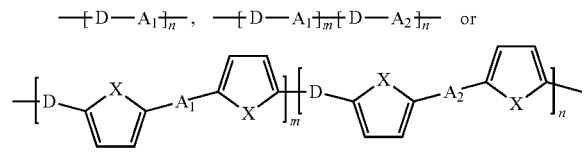

wherein D is a donor monomeric species described herein, $A_1$ and $A_2$ are acceptor monomeric species described herein. In some embodiments, m and n range from 1 to 100.

Conjugated polymeric species of the photo-thermal polymeric component, in some embodiments, have sufficient molecular weight to red-shift the absorption profile of the conjugated polymeric species into the red region of the visible spectrum and/or into the near infrared region. In some embodiments, for example, a conjugated polymeric species of the photo-thermal polymeric component has a number average molecular weight ($M_n$) of at least 7500. Molecular weight of a polymeric species in the photo-thermal polymeric component, in some embodiments, is selected from Table I.

TABLE I

| Conjugated Photo-thermal Polymer Molecular Weight (Number Average) |
| --- |
| 5500-25000 |
| 6000-20000 |
| 7500-17000 |
| 9000-16000 |
| 10000-15000 |

FIG. 3 illustrates absorption spectra red-shifting of PCPDT-BSe with increasing number average molecular weight according to one embodiment described herein.

B. Photoluminescent Polymeric Component

As described herein, the composite nanoparticle also comprises a photoluminescent polymeric component. A photoluminescent polymeric component is operable to emit light when irradiated with radiation falling within the absorption profile of the photoluminescent polymeric component. The photoluminescent polymeric component can comprise one or more polymeric species. Polymeric species of the photoluminescent component, in some embodiments, are conjugated polymeric species. Any suitable photoluminescent conjugated polymeric species may be employed in the photoluminescent polymeric component. Photoluminescent polymeric species can exhibit fluorescence or phosphorescence. In some embodiments, conjugated polymeric species emitting in the visible region of the electromagnetic spectrum can be used in the photoluminescent polymeric component. Bandgap and associated photoluminescence of the polymeric component can be tailored to spectral requirement(s) of a particular application. In some embodiments, photoluminescence of conjugated polymeric species can be in the near ultraviolet region or infrared region of the electromagnetic spectrum. Further, the spectral response of the photoluminescent polymeric component can be broadened or narrowed by the use of multiple polymeric species or a single polymeric species respectively.

Any photoluminescent conjugated polymer not inconsistent with the objectives of the present invention can be used in the photoluminescent polymeric component. In some embodiments, the conjugated polymer is a homopolymer. For example, a homopolymer can be constructed of a donor monomeric species (D), wherein D is a monocyclic, bicyclic or polycyclic arylene or monocyclic, bicyclic or polycyclic heteroarylene. The arylene structures, in some embodiments, can be fused or linked. A conjugated homopolymer, in some embodiments, is constructed of a monomer selected from the group consisting of aniline, pyrrole, thiophene, 3-substituted thiophene, bithiophene, terthiophene, selenophene, 3-substituted selenophene, isothianaphthene, p-phenylenevinylene, ethylenedioxythiophene, propylenedioxythiophene, 2,7-fluorene, substituted 2,7-fluorene, 2,7-carbazole, substituted 2,7-carbazole, thieno[3,2-b]thiophene, thieno[3,4-b]thiophene, dithienothiophene, cyclopenta[2,1-b:3,4-b']dithiophene, substituted cyclopenta[2,1-b:3,4-b']dithiophene, dithieno[3,2-b:2',3'-d]silole, benzo[1,2-b;4,5-b']dithiophene, benzo[1,2-b;3,4-b']dithiophene, indolo[3,2-b]carbazoles, dithieno[3,2-b:2',3'-d]pyrrole, diketopyrrolopyrrole, pentacene, heptacene and perylenediimine. Some suitable donor monomeric species are further illustrated in FIG. 1. In the structures of FIG. 1, X can be O, N, S or Se. In some embodiments comprising more than one X, each X can independently be O, N, S or Se. In addition, R, $R_1$, $R_2$ and $R_3$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms.

Additionally, a conjugated homopolymer of the photoluminescent polymeric component can be constructed of an acceptor monomeric species (A, $A_1$, $A_2$, $A_3$ in formula herein), wherein the acceptor monomeric species is a monocyclic, bicyclic or polycyclic arylene or monocyclic, bicyclic or polycyclic heteroarylene. The arylene structures, in some embodiments, can be fused or linked. A water insoluble conjugated homopolymer, in some embodiments, is constructed of a monomer selected from the group consisting of pyrrole, aniline, thiophene, ethlyenedioxythiophene, p-phenylenevinylene, benzothiadiazole, pydridinethiadiazole, pyridineselenadiazole, benzoxadiazole, benzoselenadiazole, thieno[3,4-b]pyrazine, thieno[3,4-b]thiophene, thieno[3,2-b]thiophene, [1,2,5]thiadiazolo[3,4-g]quinoxaline, pyrazino[2,3-g]quinoxaline, thienopyrrolidinone and isothianaphthene. Some suitable acceptor monomeric species are further illustrated in FIG. 2. In the structures of FIG. 2, X can be O, N, S or Se. In some embodiments comprising more than one X, each X can independently be O, N, S or Se. In addition, R, $R^1$ and $R^2$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms.

Alternatively, in some embodiments, a conjugated polymer of the photoluminescent component is a copolymer of two or more repeating units. For example, a conjugated polymer can be constructed of two or more monomeric species selected from the group consisting of D and A monomeric species described herein. In some embodiments, conjugated polymer is a copolymer of a donor-acceptor (D-A) architecture. For example, a D-A conjugated polymer can be composed of cyclopentadithiophene and 2,1,3-benzothiadiazole (PCPDTBT), cyclopentadithiophene and 2,1,3-benzoselenadiazole (PCPDTBSe) or poly[9,9-dihexyl-fluorene)-co-2,1,3-benzothiadiazole-co-4,7-di(thiophen-2-yl)-2,1,3-benzothiadiazole) (PFBTDBT10) In some embodiments, a water insoluble conjugated polymer has the structure of Formula (I):

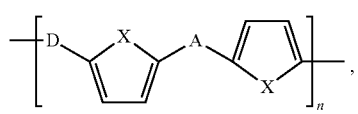

(I)

wherein D is a donor monomeric species described herein, A is an acceptor monomeric species described herein, and each X is independently O, N, S, Se or Te. In some embodiments, a D-A conjugated polymer of the photoluminescent component is of formula:

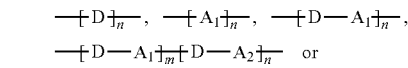

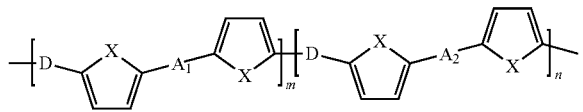

wherein D is a donor monomeric species described herein, $A_1$ and $A_2$ are acceptor monomeric species described herein. In some embodiments, m and n range from 1 to 100.

Conjugated polymeric species of the photoluminescent polymeric component, in some embodiments, have molecular weight commensurate with an emission profile in the visible region of the electromagnetic spectrum. In some embodiments, for example, a conjugated polymeric species of the photoluminescent polymeric component has a number average molecular weight ($M_n$) of at least less than 5000. Molecular weight of a polymeric species in the photoluminescent polymeric component, in some embodiments, is selected from Table II.

TABLE II

| Conjugated Photoluminescent Polymer Molecular Weight (Number Average) |
|---|
| 500-5000 |
| 1000-4500 |
| 2000-4000 |
| 500-1000 |
| 1000-2000 |

Figure 4:
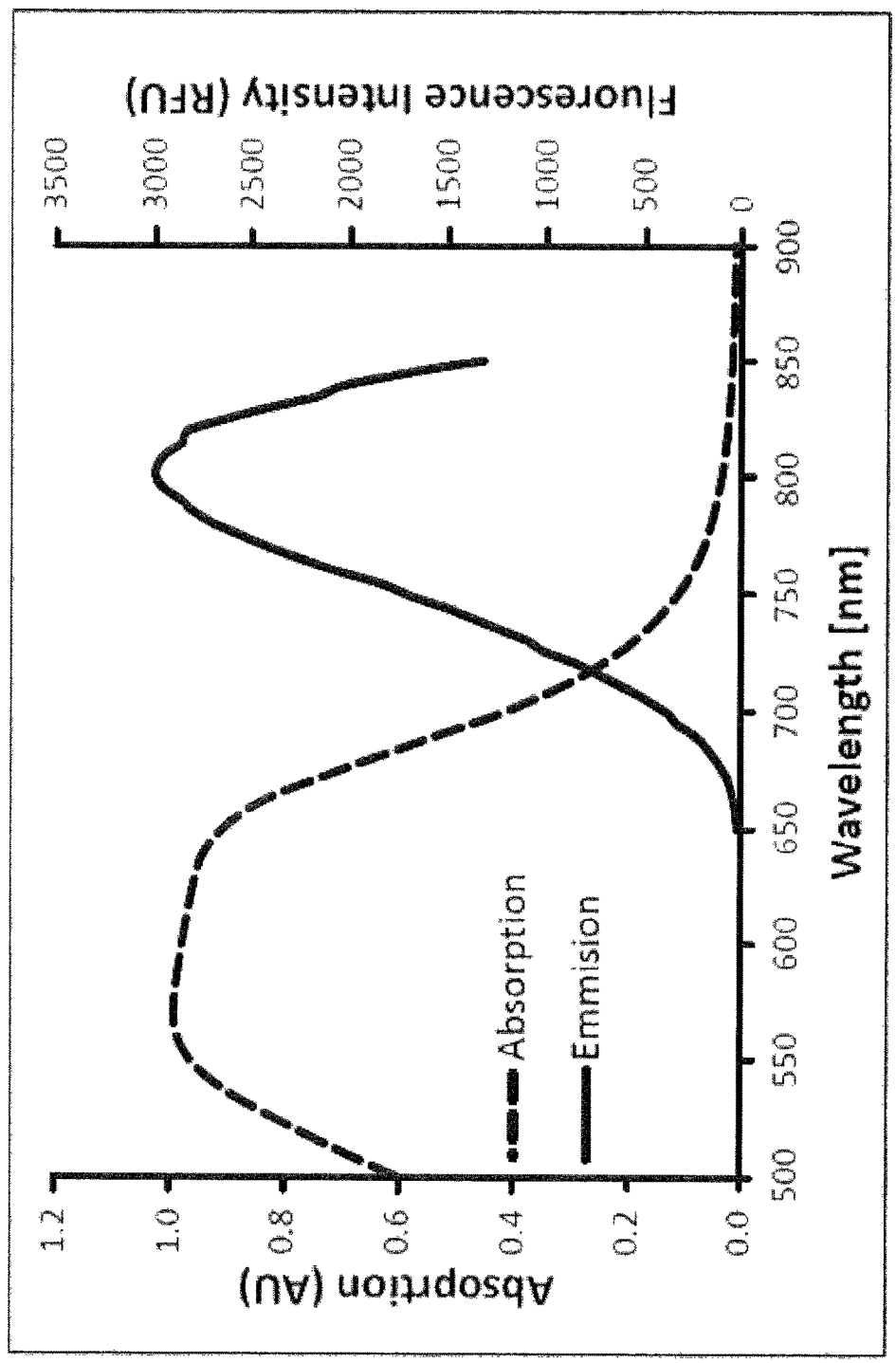
FIG. 4 illustrates absorption and emission spectra of low molecular weight photoluminescent conjugated polymer (PCPDTBSe) of a photoluminescent polymeric phase according to one embodiment described herein.

FIG. 4 illustrates absorption and emission spectra of low molecular weight photoluminescent conjugated polymer (PCPDTBSe) of a photoluminescent polymeric phase according to one embodiment described herein.

The photo-thermal polymeric component and the photoluminescent polymeric component, in some embodiments, are constructed of the same conjugated polymeric species with the principle difference being the molecular weights of the conjugated polymeric species for each component. As provided in Tables I and II herein, conjugated polymer of the photo-thermal component can have higher molecular weight than the same or similar conjugated polymer of the photoluminescent component. The difference in molecular weight permits conjugated polymer of the photo-thermal component to absorb higher wavelength radiation for generating a thermal response while permitting conjugated polymer of the photoluminescent component to absorb lower wavelengths of radiation for generating a fluorescent or phosphorescent response. In some embodiments, for example, the photo-thermal polymeric component is formed of PCPDTBSe, and the photoluminescent polymeric component is also framed of PCPDTBSe wherein PCPDTBSe of the photo-thermal polymeric component has a molecular weight an order of magnitude higher than PCPDTBSe of the photoluminescent polymeric component.

Alternatively, the photo-thermal polymeric component and photoluminescent polymeric component can be formed of different conjugated polymeric species. Conjugated polymeric species for the photo-thermal component and the photoluminescent component can be selected according to several considerations including desired heating and photoluminescent response of the composite nanoparticle, application and environment of the composite nanoparticles. Embodiments described herein contemplate any combination of conjugated polymers disclosed in Sections IA and IB herein for composite nanoparticle construction.

Further, the ratio of photo-thermal polymeric component to photoluminescent polymeric component can be varied depending on the desired properties of the composite nanoparticle. The photo-thermal component can be increased or decreased depending on the desired amount of heat generation from the nanoparticle. Similarly, the photoluminescent polymeric component can be increased or decreased depending on the desired intensity of photoluminescence from the nanoparticle. Therefore, the thermal and photoluminescent properties of the nanoparticles can be tuned according to the demands of various applications. In some embodiments, the ratio photo-thermal polymeric component to photoluminescent polymeric component ranges 1:50 to 50:1. Additional ratios are provided in Table III.

TABLE III

| Ratio of Photo-thermal Polymeric Component to Photoluminescent Polymeric Component |
|---|
| 4:1 |
| 3:1 |
| 3:2 |
| 1:1 |
| 2:3 |
| 1:3 |
| 1:4 |
| 1:10 |
| 1:5 to 5:1 |
| 1:10 to 10:1 |

Figure 5:
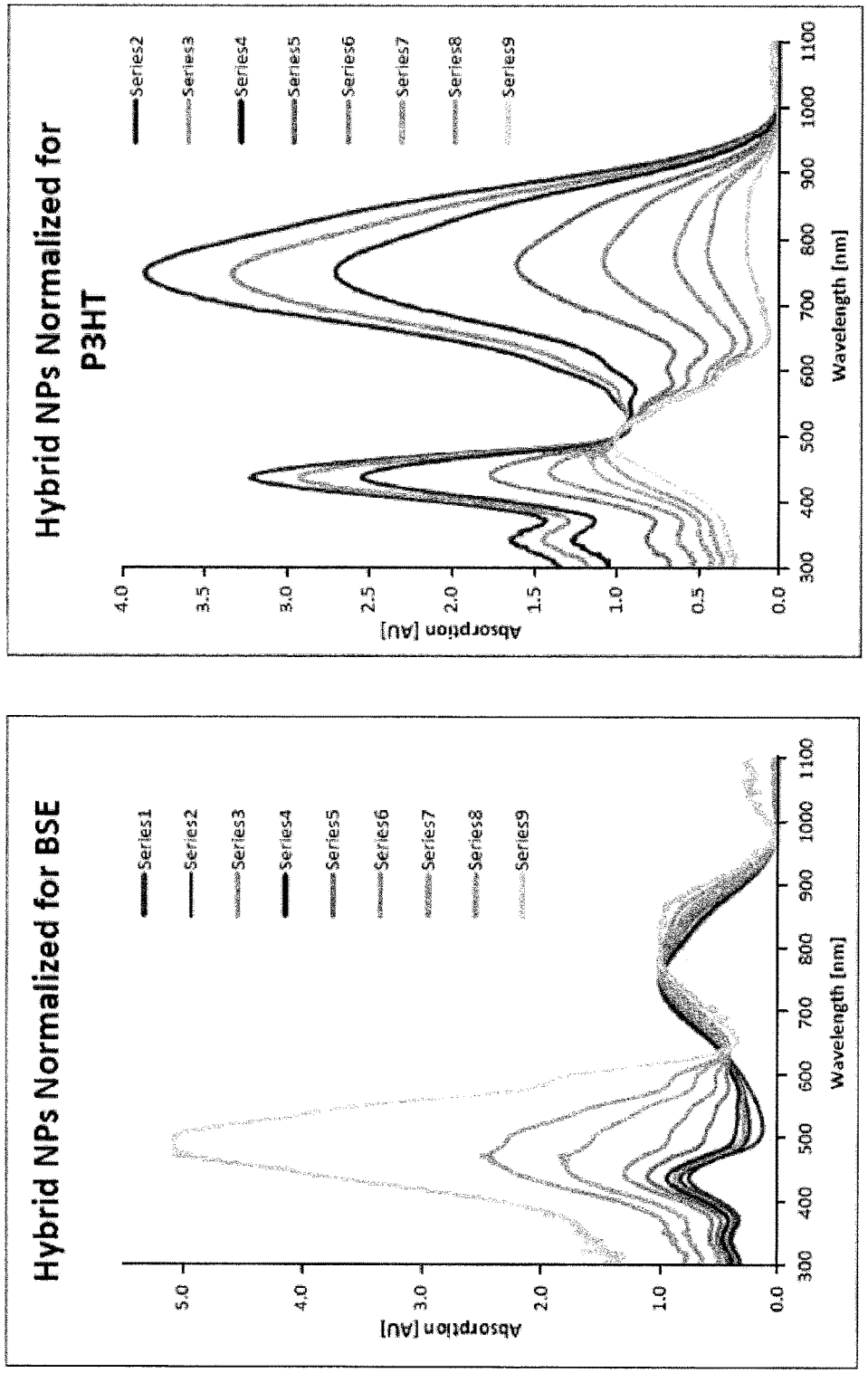
FIG. 5 illustrates normalized UV-Visible spectra of composite nanoparticles at various ratios of photo-thermal polymeric component to photoluminescent polymeric component according to some embodiments described herein.

FIG. 5 illustrates normalized UV-Visible spectra of composite nanoparticles at various ratios of photo-thermal polymeric component to photoluminescent polymeric component according to some embodiments described herein. Compositional identification of Series 2-9 of the UV-Visible spectra of FIG. 5 are provided in Table IV.

TABLE IV

| Series 2-9 Ratio and Compositional Identification | | | |
|---|---|---|---|
| Series | Ratio | Photo-thermal polymeric component (PCPDTBSe) - [mg/ml] | Photoluminescent Polymeric Component (P3HT) - [mg/ml] |
| 2 | 4:1 | 0.40 | 0.10 |
| 3 | 3:1 | 0.375 | 0.125 |
| 4 | 3:2 | 0.30 | 0.20 |
| 5 | 1:1 | 0.35 | 0.25 |
| 6 | 2:3 | 0.20 | 0.30 |
| 7 | 1:3 | 0.125 | 0.375 |
| 8 | 1:4 | 0.10 | 0.40 |
| 9 | 1:10 | 0.05 | 0.45 |

Further, the composite nanoparticle can have different architectures. In some embodiments, the photoluminescent polymeric component and the photo-thermal polymeric component are dispersed throughout the composite nanoparticle. In such embodiments, the composite nanoparticles are termed to have a hybrid architecture as referenced in FIG. 5. In other embodiments, the photoluminescent polymeric component and the photo-thermal polymeric component are localized to different regions of the composite nanoparticle. For example, the photo-thermal polymeric component can be localized to the core of composite nanoparticle and the photoluminescent component localized to surface or exterior regions of the composite nanoparticle. Localization of the photo-thermal component to the core of the composite nanoparticle with localization of the photoluminescent component to surface or exterior regions can result in core-shell architectures.

A composite nanoparticle can have any size not inconsistent with the objectives of the present invention. In some embodiments, a composite nanoparticle has particle size in the range of 0.1 nm to 500 nm. A composite nanoparticle can have a size selected from Table V.

TABLE V

| Composite Nanoparticle Size (nm) |
|---|
| 1-500 |
| 10-300 |
| 10-200 |
| 15-180 |
| 20-150 |
| 5-100 |

Figure 6:
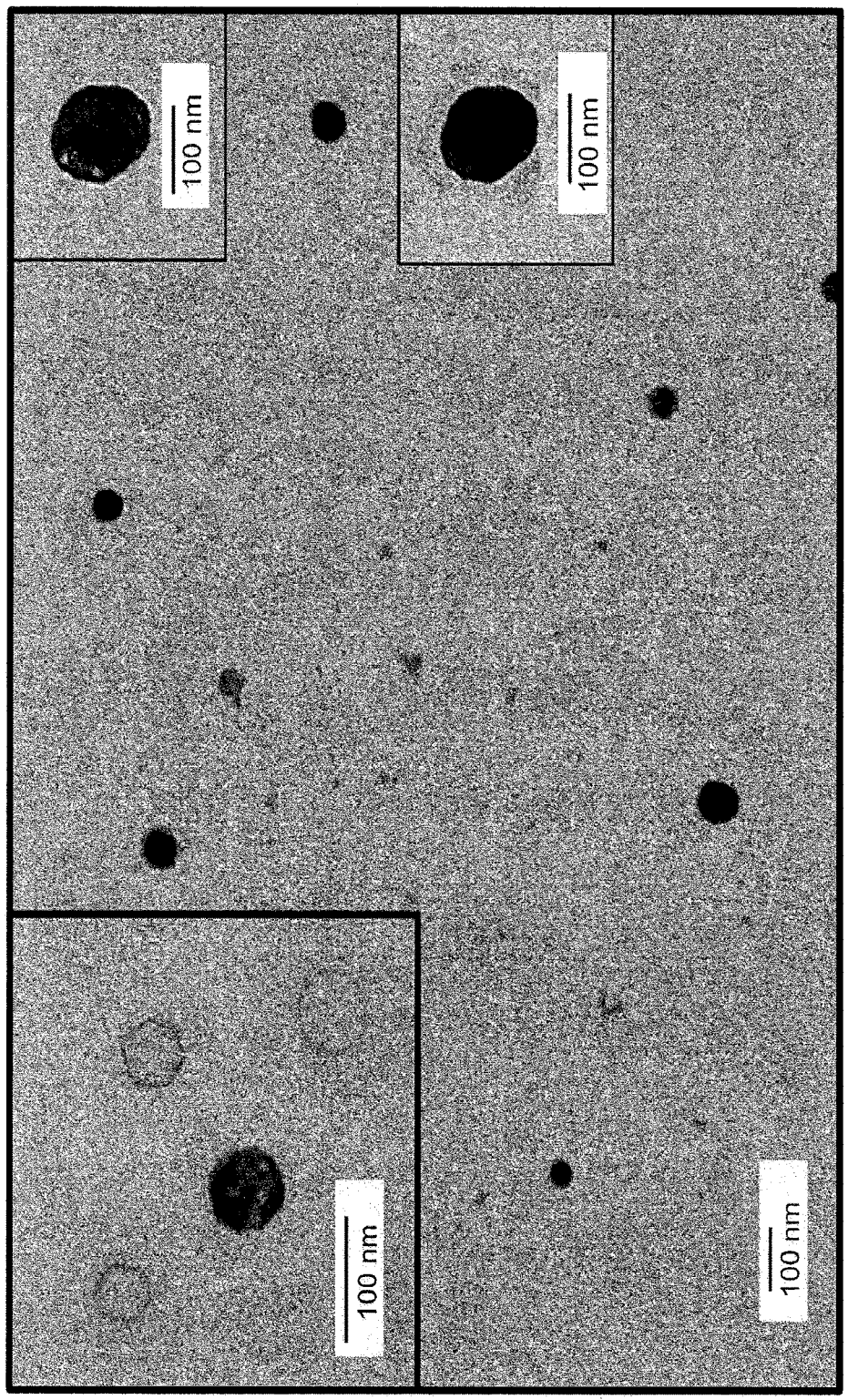
FIGS. 6 and 7 are transmission electron microscopy (TEM) images of hybrid and core-shell composite nanoparticles according to some embodiments described herein.
Figure 7:
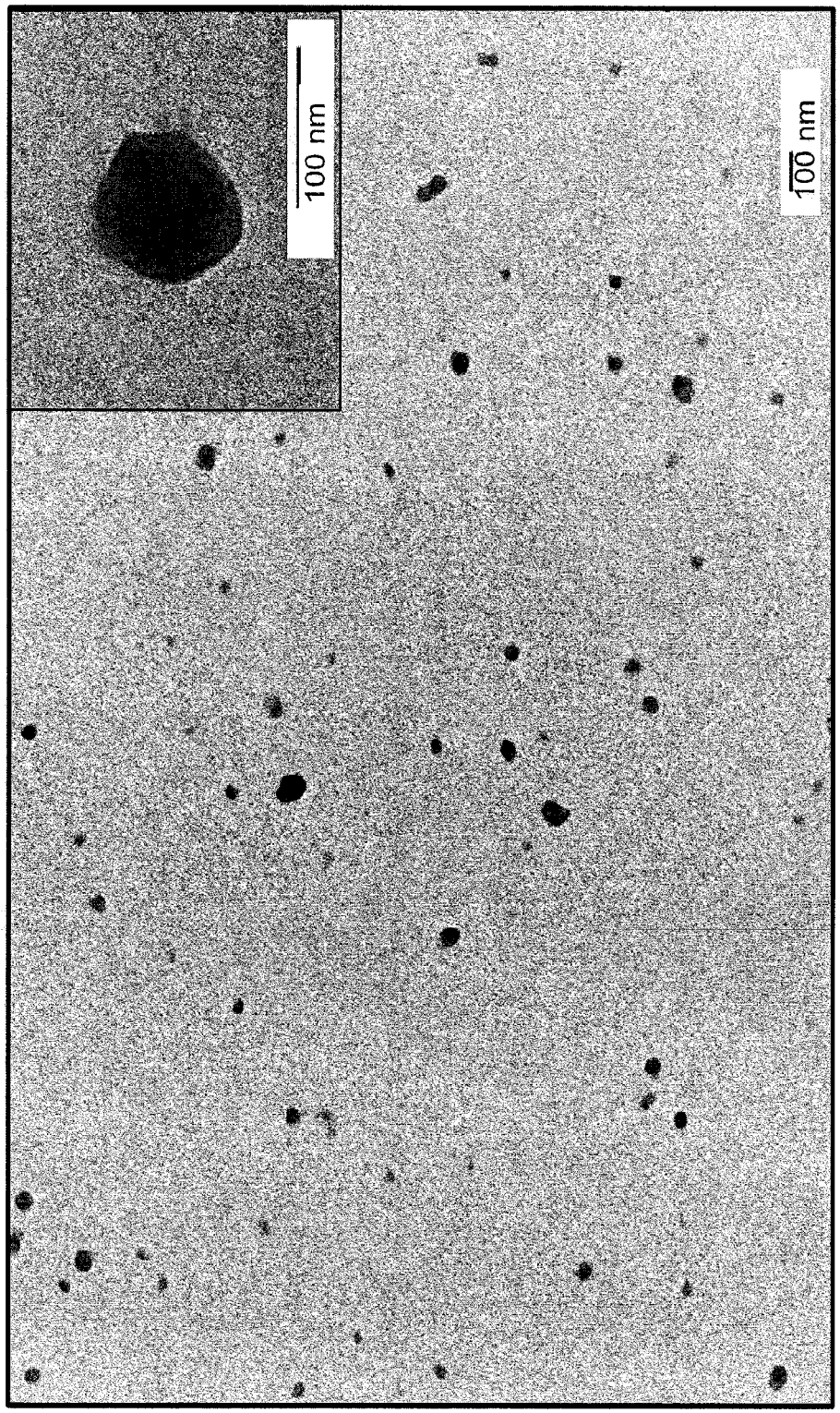

FIGS. 6 and 7 are transmission electron microscopy (TEM) images of hybrid and core shell composite nanoparticles according to some embodiments described herein. The composite nanoparticles of FIGS. 6 and 7 employ a photo-thermal component of high molecular weight PCPDTBSe and a photoluminescent component of lower molecular weight PCPDTBSe.

Composite nanoparticles described herein, in some embodiments, are modified with one or more active agents, such as one or more targeting agents. An active agent can be associated with a composite nanoparticle in any manner not inconsistent with the objectives of the present invention. For example, in some embodiments, an active agent is associated with a composite nanoparticle through one or more of hydrogen bonding, electrostatic bonding, ionic bonding, dipole-dipole forces, and van der Waals interactions. In other embodiments, the active agent is associated with the composite nanoparticle through one or more covalent bonds. Depending on composite nanoparticle construction, active agent(s) can be associated with the photo-thermal polymeric component, photoluminescent polymeric component or both. Alternatively, one or more linker structures may be used to associate active agent(s) with composite nanoparticles described herein. Any linker structure not inconsistent with the objectives of the present invention may be used. For example, polysaccharide linker structures such as chitosan can be employed. In some embodiments, linker structures are coatings on the composite nanoparticles. For example, composite nanoparticles can include an O-carboxymethyl chitosan (O-CMC) coating.

In some embodiments, an active agent comprises a targeting agent. Any targeting agent not inconsistent with the objectives of the present invention may be used. A targeting agent can comprise an antibody, a chemokine receptor, and/or a targeting ligand such as CXCR12 or CXCR4. For example, composite nanoparticles can have an O-CMC coating and associated antibody targeting agent.

Figure 8:
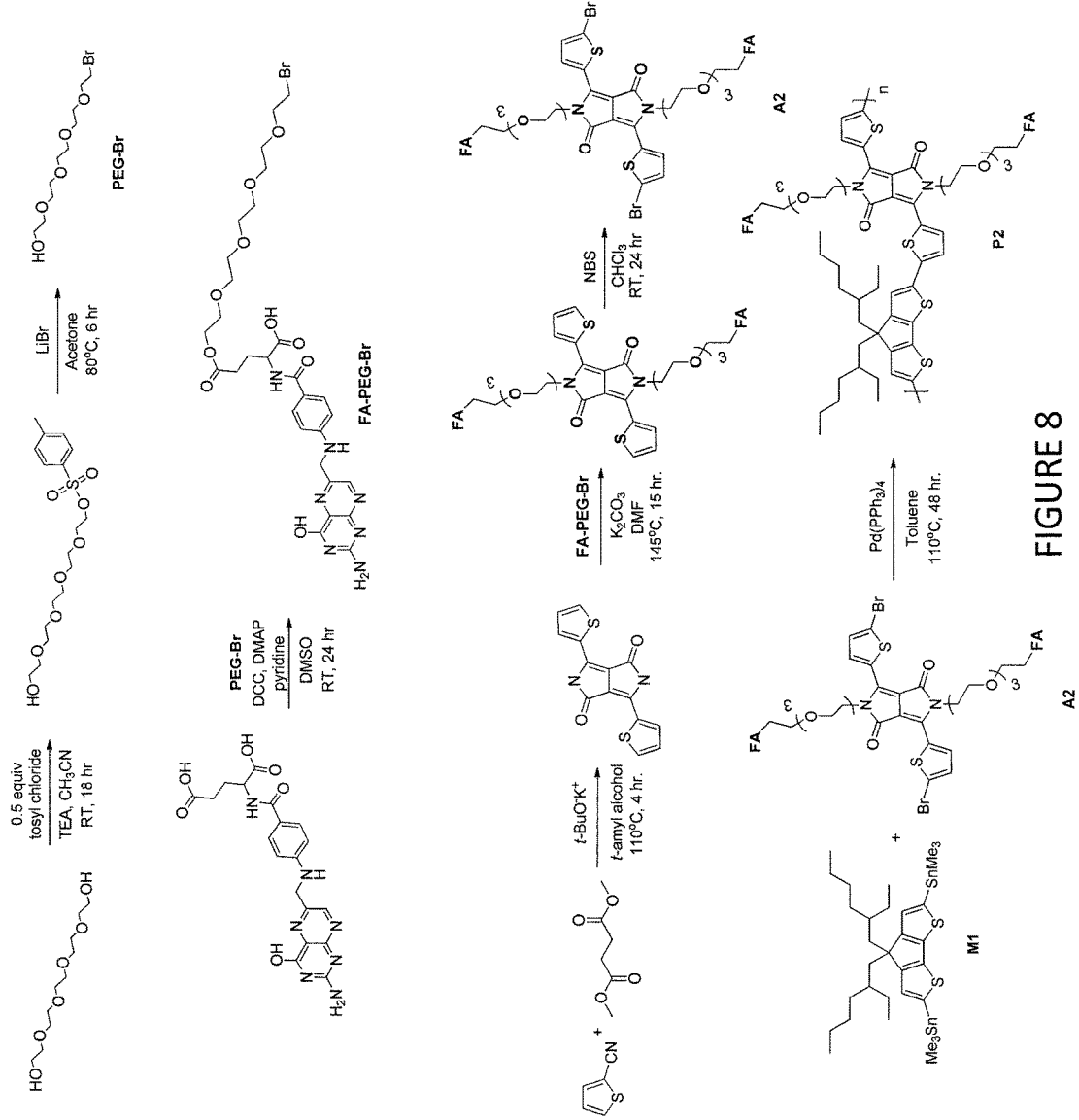
FIG. 8 illustrates a synthetic scheme for producing a folic acid modified photo-thermal polymer or photoluminescent polymer of a composite nanoparticle according to one embodiment described herein.

In some embodiments, a targeting agent comprises a nucleic acid. A nucleic acid, in some embodiments, comprises DNA. In some embodiments, a nucleic acid comprises RNA, including but not limited to siRNA. Further, a nucleic acid can have any structure or morphology not inconsistent with the objectives of the present invention. In some embodiments, for instance, a nucleic acid has a spherical or helical morphology. In addition, in some embodiments, a targeting agent comprises folic acid. FIG. 8 illustrates a synthetic scheme for producing a folic acid modified photothermal polymer or photoluminescent polymer of a composite nanoparticle according to one embodiment described herein.

In some embodiments, an active agent comprises a compound that can facilitate binding of a composite nanoparticle to a tumor, biofilm, bacterial matrix, or extracellular matrix. For example, in some embodiments, an active agent comprises a glucan or glycan such as dextran, dextran sulfate, heparin or heparin sulfate; a structural protein such as laminin; an amino acid such as lysine; and/or a growth factor such as vascular endothelial growth factor (VEGF) or fibroblast growth factor (FGF). Alternatively, composite nanoparticle compositions described herein can be systemically administered and localize in disease tissue, such as cancerous tissue, without use of any targeting agents.

Further, in some embodiments, an active agent comprises a compound that can degrade or substantially degrade one or more extracellular matrix components. For example, in some embodiments, an active agent comprises an enzyme. Any enzyme not inconsistent with the objectives of the present invention may be used. In some embodiments, for example, an enzyme comprises collagenase, trypsin or papain. Additionally, an active agent can comprise pharmaceutical agents, chemotherapeutic agents, antiviral agents or antimicrobial agents or combinations thereof. Interestingly, composite nanoparticles described herein can demonstrate antimicrobial activity in an as-formed or unmodified form. Active agents can be associated with surfaces and/or interior regions of the composite nanoparticles. In some embodiments, composite nanoparticles serve as vehicles for transport of active agents to sites of tissue treatment. For example, in some embodiments, the composite nanoparticles comprise a chemotherapeutic, antibiotic, antiviral or other pharmaceutical agent for delivery to diseased tissue.

The composite nanoparticles can be heated to accelerate uptake of the chemotherapeutic or other pharmaceutical agent by the diseased tissue.

As described herein, the photo-thermal polymeric component and/or photoluminescent polymeric component of compositions and methods described herein can be substituted by a photo-thermal oligomeric component and/or photoluminescent oligomeric component. Similarly, the photo-thermal polymeric component and/or photoluminescent polymeric component of compositions and methods described herein can be also substituted by a photo-thermal small molecule component and/or photoluminescent small molecule component. Suitable oligomers and small molecules for serving as the photoluminescent component and/or photo-thermal component, in some embodiments, are of formula:

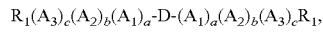

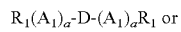

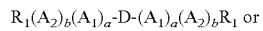

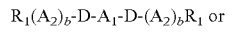

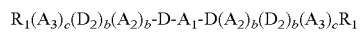

wherein $R_1$, $A_1$, $A_2$, $A_3$, D and $D_2$ are defined in this Section I and FIGS. 1 and 2 and a, b, c are integers from 1-5.

For example, photoluminescent oligomeric component can include oligomeric PCPDTBSe. Oligomeric PCPDTBSe, in some embodiments has molecular weight of 100-500 Da. In some embodiments, oligomeric PCPDTBSe is obtained from the synthesis of polymeric PCPDTBSe. The polymeric synthesis produces an oligomeric PCPDTBSe fraction that can be captured by one or more chromatographic or separation techniques. Moreover, the photoluminescent oligomeric component can comprise poly[9,9-dihexylfluorene)-co-2,1,3-benzothiadiazole-co-4,7-di(thiophen-2-yl)-2,1,3-benzothiadiazole) (PFBTDBT10) or oligomeric P3HT. Further, suitable small molecules can be of formula:

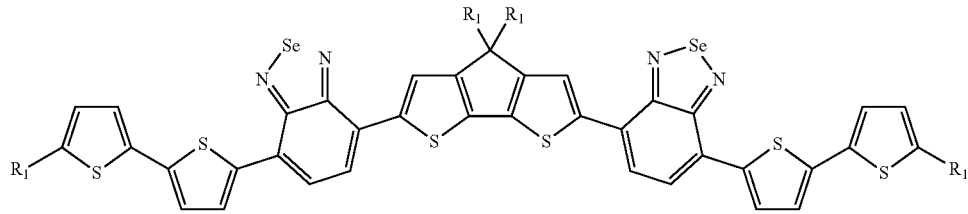

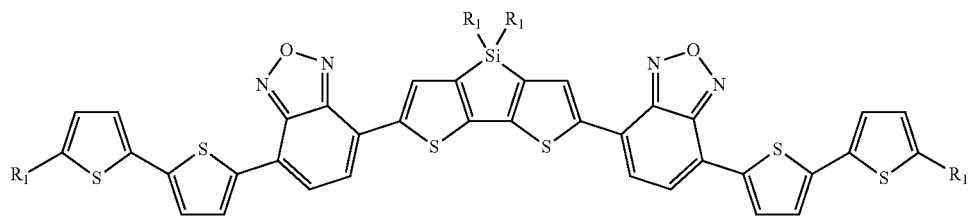

-continued

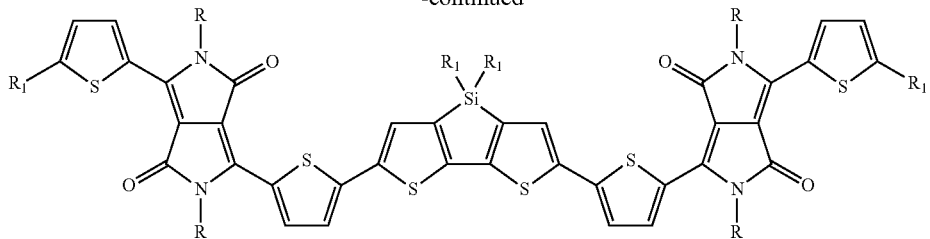

II. Compositions Comprising Composite Nanoparticles

In another aspect, compositions comprising composite nanoparticles are described herein. A composition, in some embodiments, comprises an aqueous or aqueous-based medium and composite nanoparticles disposed in the aqueous or aqueous-based medium, the composite nanoparticles comprising a photoluminescent polymeric component and a photo-thermal polymeric component. The composite nanoparticles, in some embodiments, are dispersed in the aqueous or aqueous-based medium. Alternatively, the composite nanoparticles are solubilized in the aqueous or aqueous-based medium. Composite nanoparticles disposed in the aqueous or aqueous-based medium can have any construction and/or properties described in Section I herein. As set for the in the examples, below, the composite nanoparticles can comprise one or more surface species, such as surfactant, to enhance dispersion in the aqueous or aqueous based medium.

Composite nanoparticles can be present in the aqueous or aqueous-based medium in any amount not inconsistent with the objectives of the present invention. For example, composite nanoparticles can be present in the aqueous or aqueous-based medium in an amount of 1 fg to 1 mg. In some embodiments, composite nanoparticles are present in the aqueous or aqueous-based medium in an amount selected from Table VI.

TABLE VI

| Composite Nanoparticles in Aqueous or Aqueous-based Medium Amount (µg/ml) |
|---|
| 5-500 |
| 10-200 |
| 15-150 |
| 20-120 |
| 10-100 |
| 500-1,000 |
| >1,000 |

A composition described herein comprising composite nanoparticles can demonstrate an increase in temperature when irradiated with electromagnetic radiation of wavelength matching or substantially matching the absorption spectrum of the photo-thermal polymeric component, the increase in temperature being at least five times or at least ten times greater than an increase in temperature of water irradiated under conditions matching the conjugated polymer irradiation, wherein the composite nanoparticles are present in an amount ranging from about 1 fg/ml to about 100 mg/ml. In some embodiments, the increase in temperature is at least 15 times or 20 times greater than an increase in temperature of water irradiated under matching conditions. Further, in some embodiments, composite nanoparticles are present in an amount ranging from about 5 µg/ml to about 120 µg/ml, from about 5 µg/ml to about 30 µg/ml, from about 30 µg/ml to about 50 µg/ml or from about 50 µg/ml to about 100 µg/ml to provide any of the foregoing temperature increases.

Figure 9:
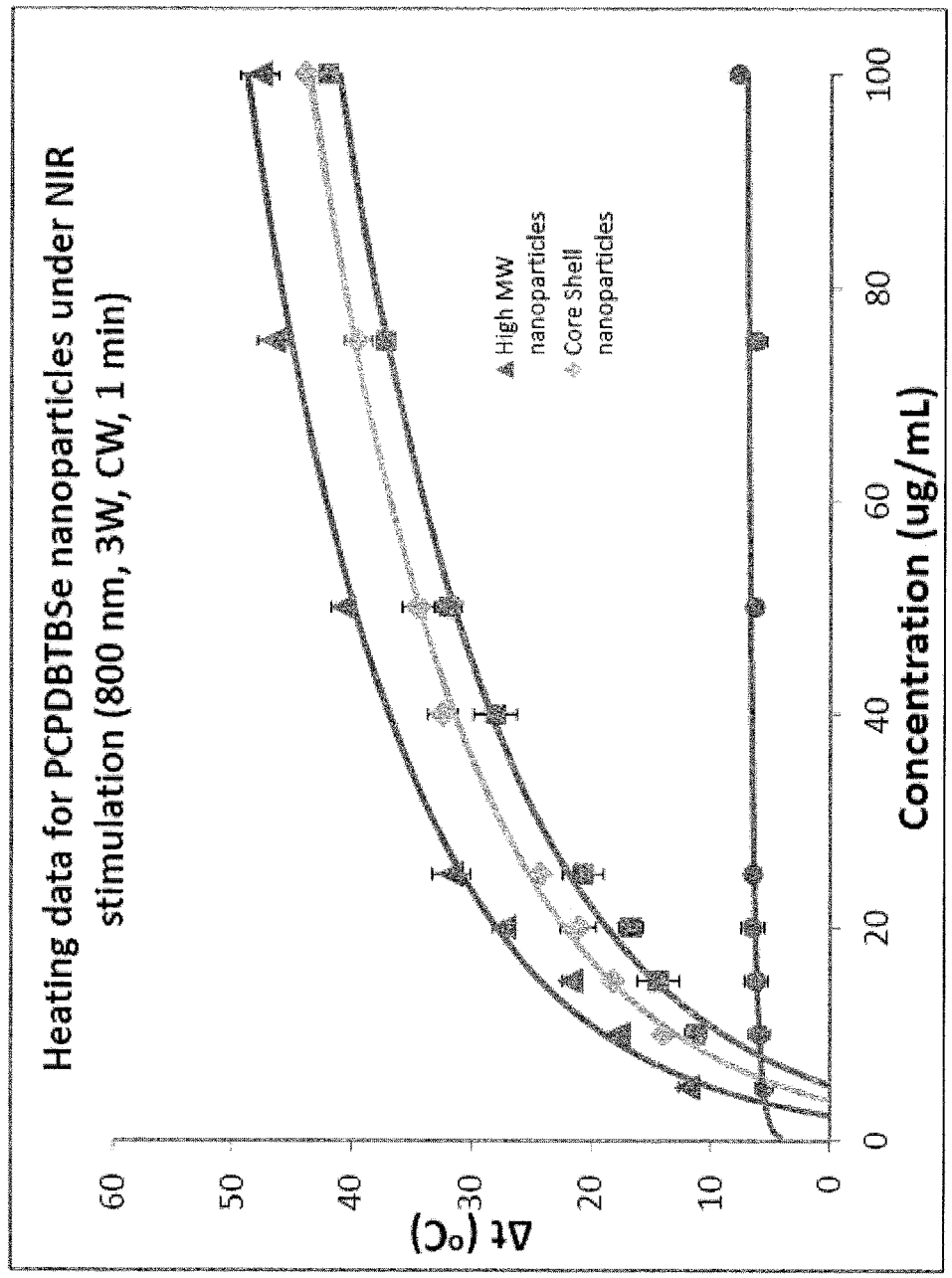
FIG. 9 illustrates heating data of aqueous compositions comprising composite nanoparticles at various concentrations according to some embodiments described herein.
Figure 10:
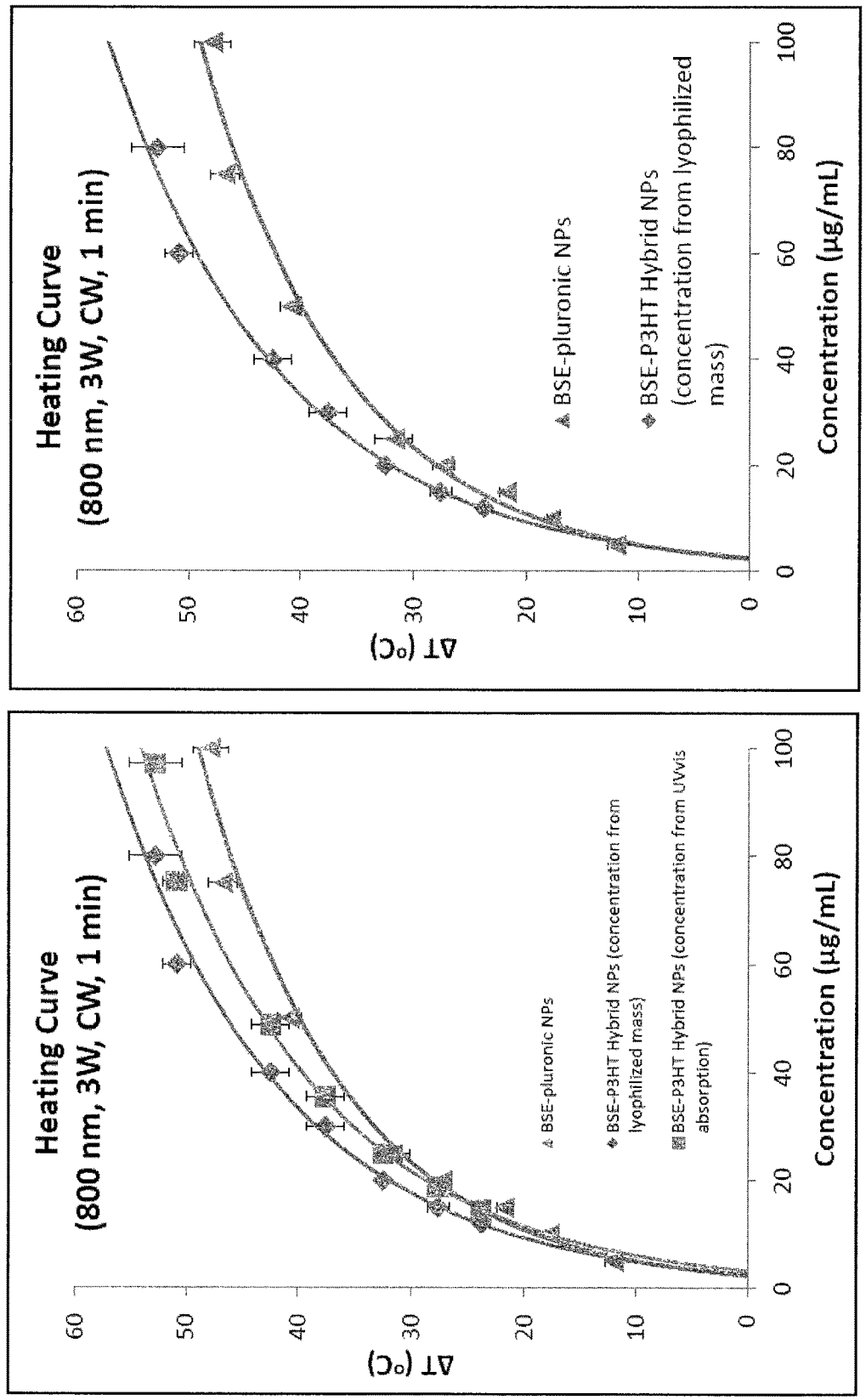
FIG. 10 illustrates additional heating curves of composite nanoparticles described herein.
Figure 11:
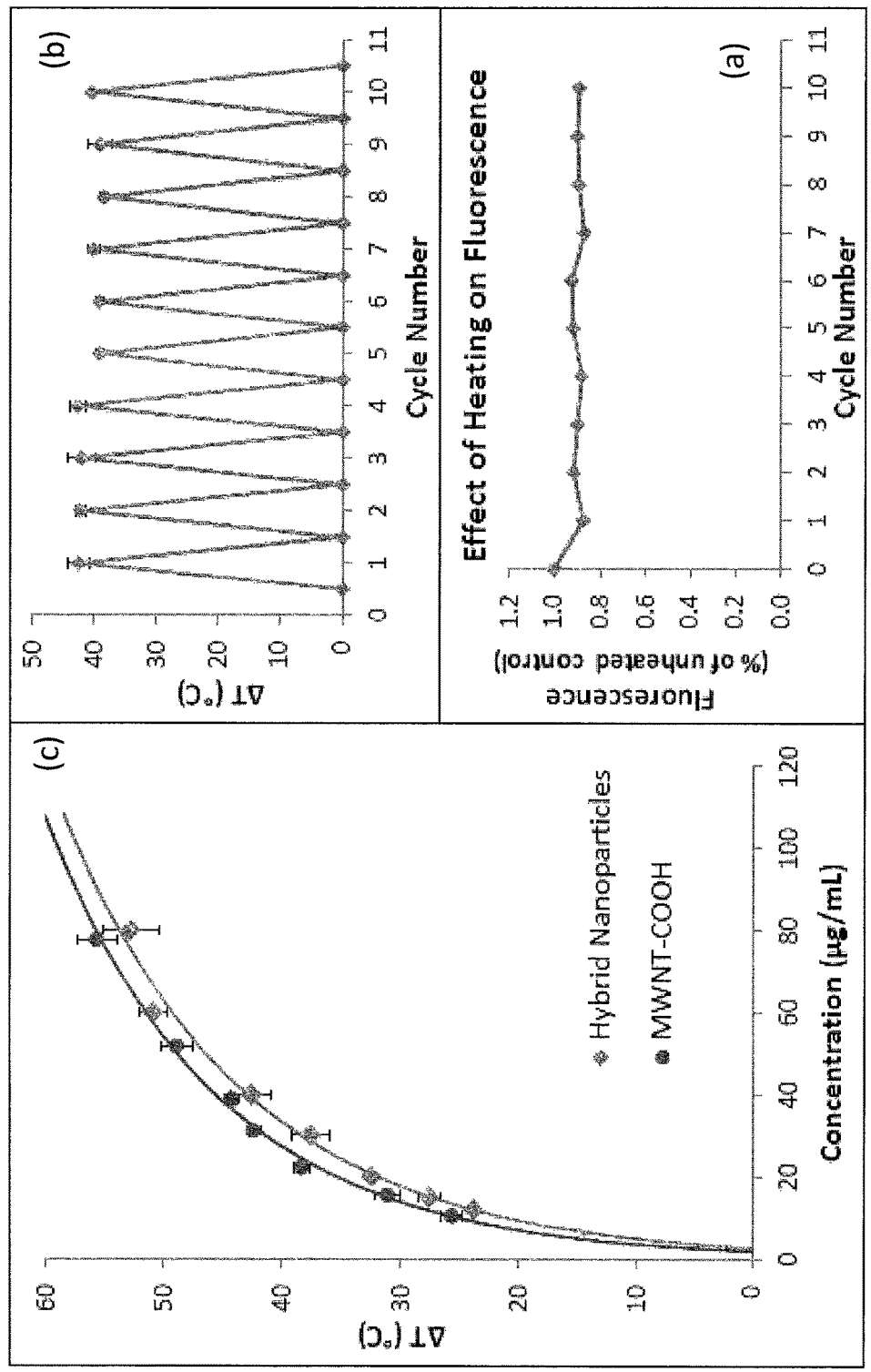
FIG. 11(a) illustrates photoluminescence of the composite nanoparticles during heating cycles according to one embodiment described herein.
FIG. 11(b) illustrates the thermal response of composite nanoparticles over several heating cycles according to one embodiment described herein.
FIG. 11(c) illustrates thermal response of composite nanoparticles according to one embodiment described herein relative to thermal response of multi-walled carbon nanotubes.

FIG. 9 illustrates heating data of aqueous compositions comprising composite nanoparticles at various concentrations according to some embodiments described herein. The composite nanoparticles of FIG. 9 were formed of a photo-thermal polymeric component of PCPDBTBSe and a photoluminescent component of higher molecular weight PCP-DBTBSe. Both core-shell and hybrid composite nanoparticle architectures demonstrates significant heating when irradiated with radiation of 800 nm. FIG. 10 illustrates additional heating curves of composite nanoparticles described herein. The composite nanoparticles of FIG. 10 exhibited a hybrid architecture wherein the photo-thermal polymeric component was formed of PCPDTBSe and the photoluminescent polymeric component was poly(3-hexyl-thiophene-2,5-diyl) [P3HT]. The thermal response of PCP-DTBSe-P3HT hybrid composite nanoparticles is reproducible permitting heat cycling of the composite nanoparticles. FIG. 11(b), for example, illustrates the thermal response of composite nanoparticle over several heating cycles. The composite nanoparticles provide nearly identical thermal responses over the ten cycles indicating thermal stability of the composite nanoparticles. Further, the thermal response of the composite nanoparticles does not substantially affect the photoluminescent response. FIG. 11(a) illustrates photoluminescence of the composite nanoparticles during heating cycles. As illustrated in FIG. 11(a), the photoluminescent response was reproducible and not substantially affected by the nanoparticle thermal response. Additionally, the composite nanoparticles of PCPDTBSe:P3HT exhibited heating performance substantially similar to multi-walled carbon nanotubes (MWNT) as provided in FIG. 11(c).

Figure 12:
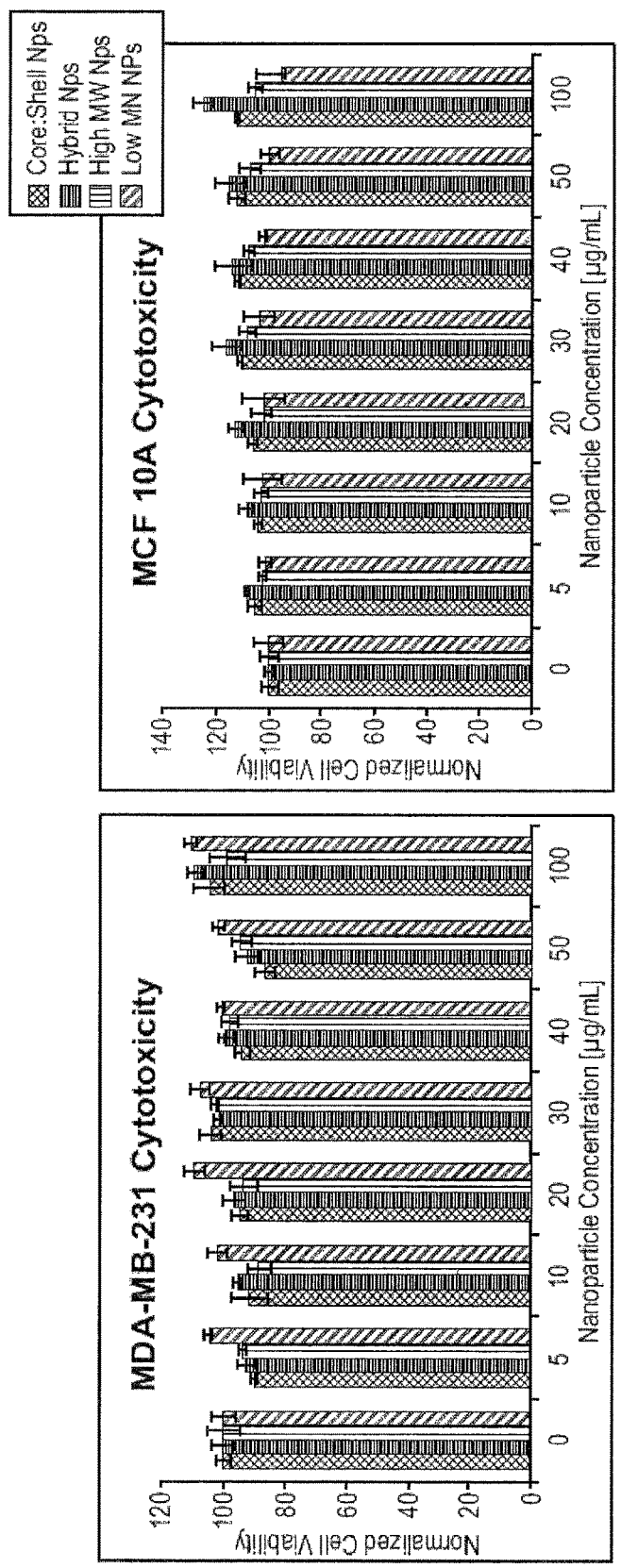
FIG. 12 illustrates the absence of cytotoxicity of composite nanoparticles with breast cancer cell lines MDA-MB-231 and MCF 10A.
Figure 13:
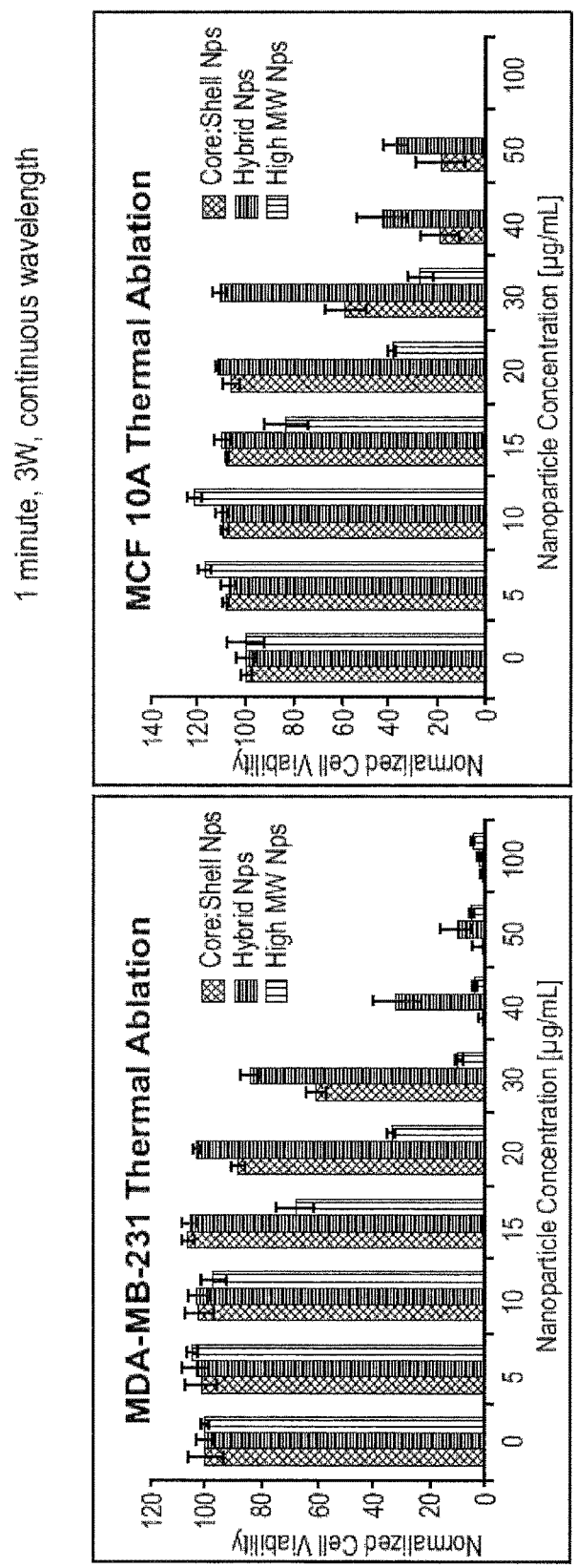
FIG. 13 illustrates thermal ablation of MDA-MB-231 and MCF 10A cell lines by composite nanoparticle compositions described herein.
Figure 23:
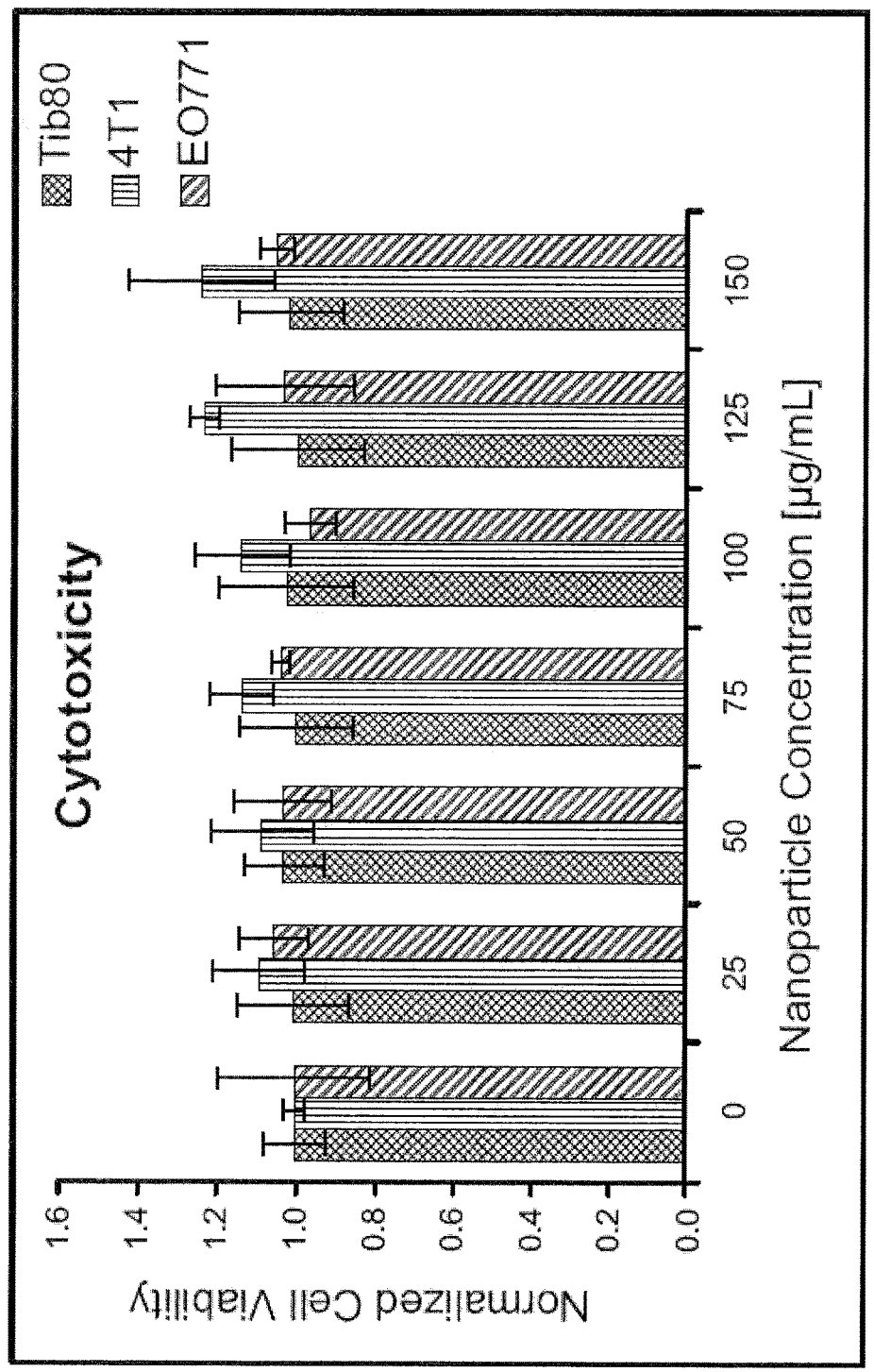
FIG. 23 illustrates results of a cytotoxicity study employing composite nanoparticles according to one embodiment described herein.

Compositions comprising aqueous or aqueous-based medium and composite nanoparticles disposed in the aqueous or aqueous-based medium, in some embodiments, do not demonstrate cytotoxicity, permitting use of the compositions in biological applications. FIG. 12 illustrates the absence of cytotoxicity of composite nanoparticle with breast cancer cell lines MDA-MB-231 and MCF 10A. The composite nanoparticles of FIG. 12 included a photo-thermal polymeric component of PCPDTBSe and a photoluminescent component also of PCPDTBSe having a lower molecular weight than that of the photo-thermal polymeric component. Additionally, both the hybrid and core-shell architectures of the composite nanoparticles did not exhibit cytotoxicity. However, the composite nanoparticles of FIG. 12 demonstrated efficient thermal ablation of the breast cancer cell lines when irradiated, as illustrated in FIG. 13. Additional cytotoxicity and ablation data is provided in FIGS. 17 and 18 for the FHS-Int74 and CT26 cell lines and FIGS. 23 and 24 for the Tib80, 4T1 and EO771 cell lines. In view of these results, compositions comprising composite nanoparticles can be employed in the treatment of diseased tissue, including cancerous tissue.

Additional compositions incorporating composite nanoparticles described herein include wound dressings. A wound dressing comprises a support phase and composite nanoparticles in contact with the support phase, the composite nanoparticles comprising a photoluminescent polymeric component and a photo-thermal polymeric component. The support phase can be formed of traditional would dressing materials including elastomeric materials, such as poly-1,8-octanediol citrate (POC). Wound dressings including composite nanoparticles described herein can provide heat to the wound when irradiated. As an alternative to composite nanoparticles, a coating comprising a photo-thermal polymeric component and photoluminescent polymeric component can be applied to the wound dressing support phase. For example, a coating comprising a photo-thermal polymeric component and photoluminescent polymeric component can be applied to fibers or other surfaces of traditional wound dressings.

III. Tissue Treatment Systems

In another aspect, tissue treatment systems are described herein. A tissue treatment system comprises a source of radiation and a composition including an aqueous or aqueous-based medium and composite nanoparticles disposed in the aqueous or aqueous-based medium, the composite nanoparticles comprising a photoluminescent polymeric component and a photo-thermal polymeric component, wherein radiation emitted by the radiation source at least partially falls within the absorption profile of the photoluminescent polymeric component, photo-thermal polymeric component or both. Composite nanoparticles for tissue treatment systems can have any construction and/or properties described in Section I herein. Further, aqueous or aqueous-based composition employing the composite nanoparticles can have any construction and/or properties described in Section II herein. In some embodiments, wound dressings described herein are used in conjunction with the radiation source to provide a tissue treatment system.

Any radiation source not inconsistent with the objectives of the present invention can be used to irradiate composite nanoparticles of tissue treatment systems. In some embodiments, a radiation source can provide radiation of sufficient bandwidth to induce a photo-thermal response in the photo-thermal polymeric component and a photoluminescent response in the photoluminescent polymeric component. Alternatively, the radiation source can provide narrow bandwidth radiation directed to the absorption profiles of the photo-thermal polymeric component and the photoluminescent polymeric component. In such embodiments, a radiation source comprises two or more radiation sources, such as two or more lasers or lamps.

Tissue to be treated by tissue treatments systems described herein can include diseased tissue, such as cancerous tissue and/or tissue infected with a microbial agent or viral agent. Alternatively, tissue can be adipose tissue and/or other tissue type commonly removed or altered during cosmetic surgery procedures. Further, tissue may include ophthalmological tissue such as retinal tissue.

IV. Methods of Making Composite Nanoparticles

Figure 14:
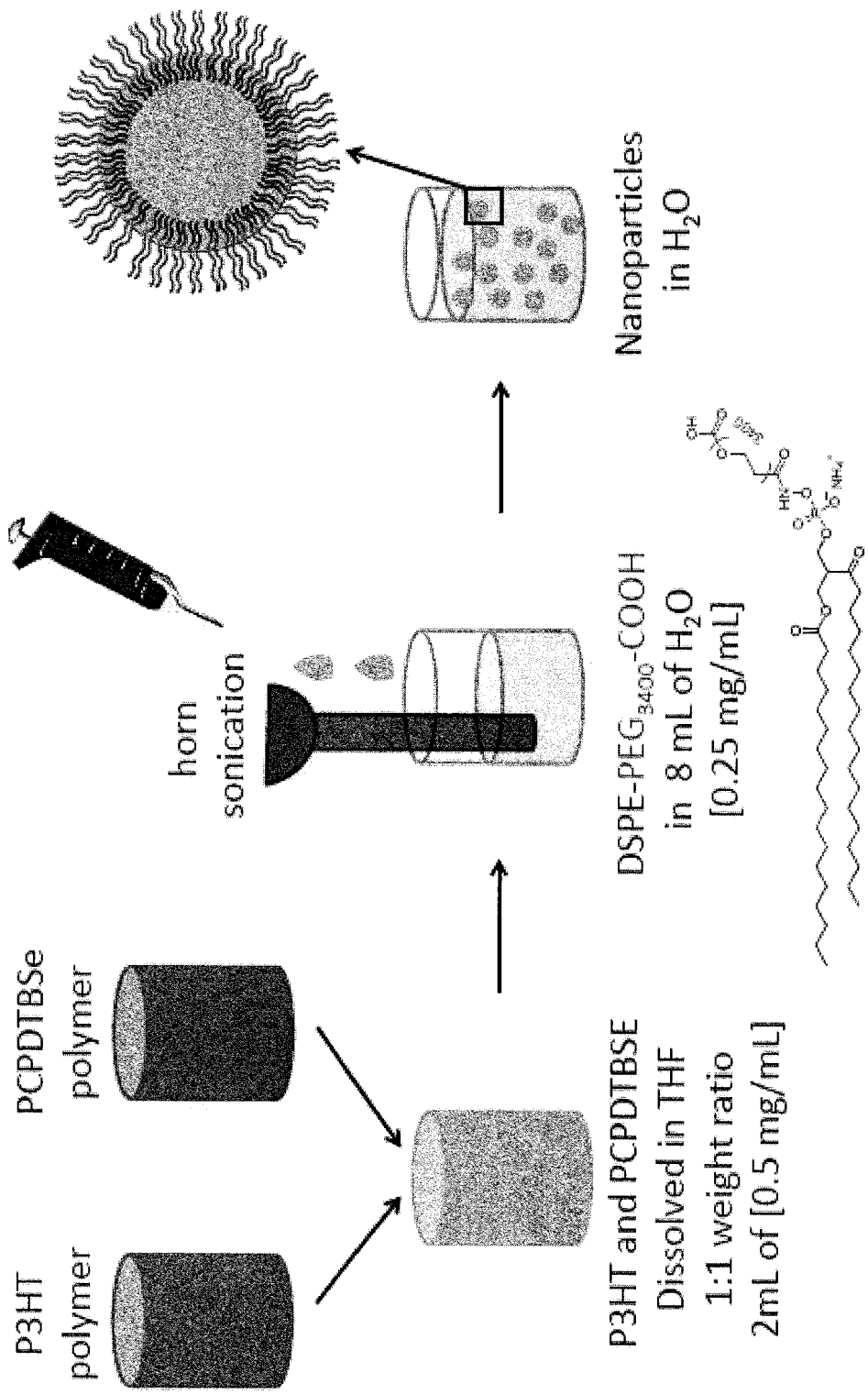
FIG. 14 illustrates a method of making composite nanoparticles according some embodiments described herein.
Figure 15:
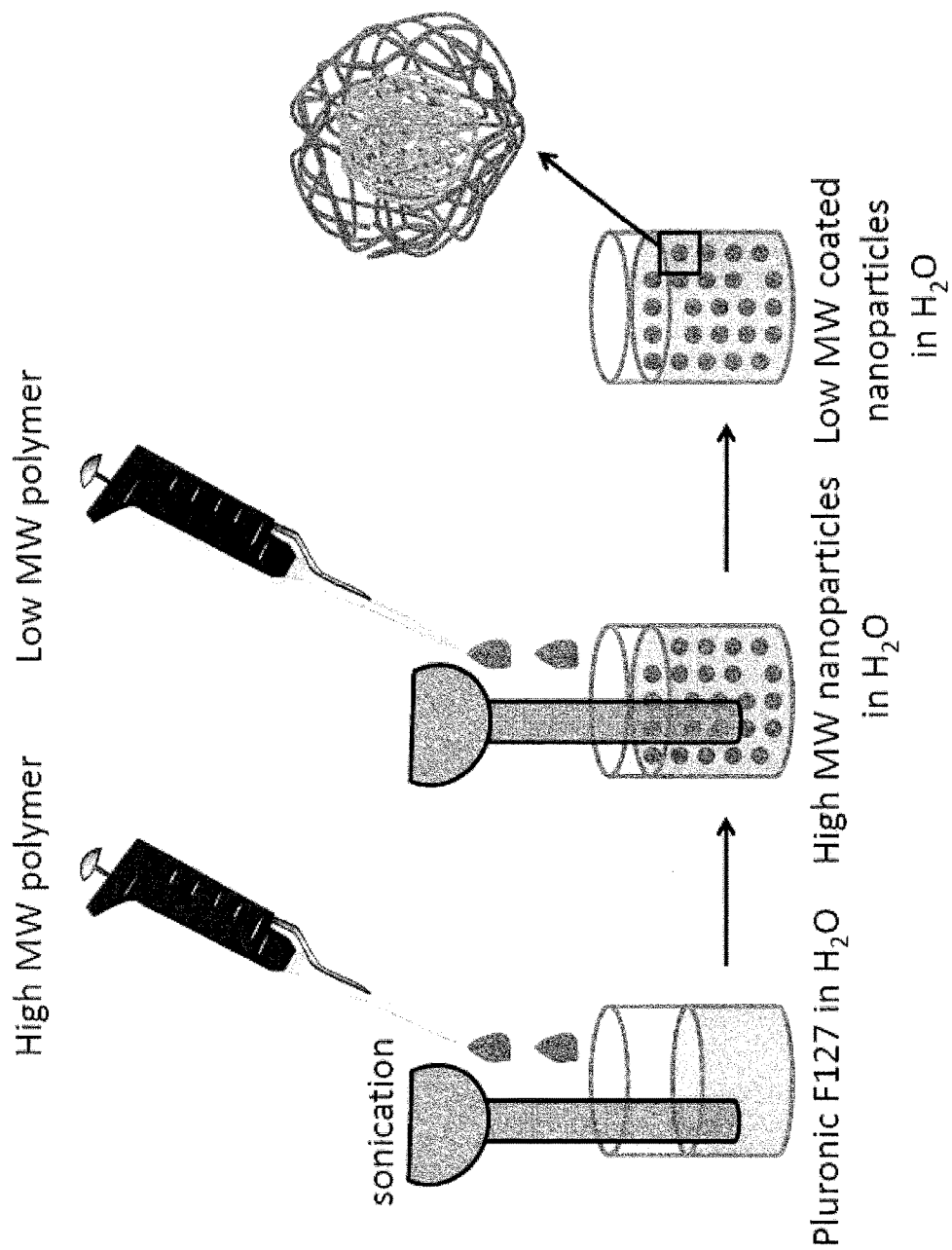
FIG. 15 illustrates a method of making composite nanoparticles according some embodiments described herein.

In addition to compositions, methods of making composite nanoparticles are described herein. A method of making composite nanoparticles comprises providing a mixture including a photoluminescent polymeric component and photo-thermal polymeric component in a liquid medium and sonicating the mixture to form the composite nanoparticles comprising the photoluminescent component associated with the photo-thermal polymeric component. In some embodiments, the photoluminescent polymeric component and the photo-thermal polymeric component are present throughout the composite nanoparticle providing a hybrid architecture. FIG. 14 illustrates the foregoing method of making composite nanoparticles having a hybrid architecture.

Alternatively, a method of making composite nanoparticles comprises providing a mixture including a photo-thermal component in a liquid medium and sonicating the mixture to form photo-thermal polymeric nanoparticles. A photoluminescent polymeric component is added to the mixture comprising the photo-thermal polymeric nanoparticles and the resulting mixture is sonicated to at least partially coat the photo-thermal polymeric nanoparticles with the photoluminescent polymeric component. In such embodiments, the composite nanoparticles can have a core-shell architecture.

In another embodiment, a method of making composite nanoparticles comprises providing a mixture including a photoluminescent polymeric component in a liquid medium and sonicating the mixture to form photoluminescent polymeric nanoparticles. A photo-thermal polymeric component is added to the mixture comprising the photoluminescent polymeric nanoparticles and the resulting mixture is sonicated to at least partially coat the photoluminescent polymeric nanoparticles with the photo-thermal polymeric component. In such embodiments, the composite nanoparticles can have a core-shell architecture.

Composite nanoparticles made according to methods described herein can have any construction and/or properties described in Section I herein. Further, sonication in methods described herein can be replaced by electrospraying, spin coating and/or printing techniques to form composite nanoparticles having constructions and/or properties described in Section I herein.

V. Methods of Treating Tissue

In a further aspect, methods of treating tissue are described herein. A method of treating tissue comprises providing a composition including an aqueous or aqueous-based medium and composite nanoparticles in the aqueous or aqueous-based medium, the nanoparticles comprising a photoluminescent polymeric component and a photo-thermal polymeric component. The composition is positioned in the tissue, and the tissue is heated by irradiating the composition with radiation at least partially falling within the absorption profile of the photo-thermal polymeric component. In some embodiments, the method further comprises determining the position of the composition by irradiating the composition with radiation at least partially falling within the absorption profile of the photoluminescent polymeric component.

Composite nanoparticles for tissue treatment systems can have any construction and/or properties described in Section I herein. Further, aqueous or aqueous-based compositions employing the composite nanoparticles can have any construction and/or properties described in Section II herein. Tissue to be treated by tissue treatments systems described herein can include diseased tissue, such as cancerous tissue and/or tissue infected with a microbial agent or viral agent. Alternatively, tissue can be adipose tissue and/or other tissue type commonly removed or altered during cosmetic surgery procedures. Further, tissue may include ophthalmological tissue, such as retinal tissue, or dental tissue.

These and other embodiments are further illustrated by the following non-limiting examples.

EXAMPLE 1—Synthesis of PCPDTBT and PCPDTBSe

All reagents were purchased from common commercial sources and used without further purification unless otherwise noted. 4H-Cyclopenta-[1,2-b:5,4-b']dithiophene was purchased from Astar Pharma. THF was dried over Na/benzophenone ketal. 4,4-Bis(2-ethylhexyl)-2,6-bis(trimethylstannyl)-4H-cyclopenta-[2,1-b;3,4-b']dithiophene, 4,7-dibromo-2,1,3-benzothiadiazole and 4,7-dibromo-2,1,3-benzoselenadiazole were synthesized according to their literature procedures (see J. Hou, T. L. Chen, S. Zhang, H.-Y. Chen, Y. Yang, *J. Phys. Chem. C* 2009, 113, 1601-1607; Z. Zhu, D. Waller, R. Gaudiana, M. Morana, D. Muhlbacher, M. Scharber, C. Brabec, *Macromolecules* 2007, 40, 1981-1986; C. W. Bird, G. W. H. Cheeseman, A. A. Sarsfield, *J. Chem. Soc.* 1963, 4767-4770; I. H. Jung, H. Kim, M.-J, Park, B. Kim, J.-H. Park, E. Jeong, H. Y. Woo, S. Yoo, H.-K. Shim, *J. Polym. Sci. Part A: Polym. Chem.* 2010, 48, 1423-1432; X. Li, W. Zeng, Y. Zhang, Q. Hou, W. Yang, Y. Cao, *Eur. Polym. 1* 2005, 41, 2923-2933; and Y. Tsubata, T. Suzuki, T. Miyashi, Y. Yamashita, *J. Org. Chem.* 1992, 57, 6749-6755, the entireties of which are hereby incorporated by reference). Poly[4,4-bis(2-ethylhexyl)-cyclopenta[2,1-b;3,4-b]dithiophene-2,6-diylalt-2,1,3-benzothiadiazole-4,7-diyl] (PCPDTBT) and poly[4,4-bis(2-ethylhexyl)-cyclopenta[2,1-b;3,4-b]dithiophene-2,6-diylalt-2,1,3-benzoselenadiazole-4,7-diyl] (PCPDTBSe) were synthesized using a Stille coupling procedure under microwave radiation. The polymerization procedure is outlined below.

Flash chromatography was performed on a Biotage Isolera™ Flash Purification System using Biotage SNAP Flash Purification Cartridges as the stationary phase. Microwave assisted polymerizations were carried out using a CEM Discover Microwave reactor. 300 and 500 MHz $^1$H-NMR spectra were recorded on Bruker Avance DPX-300 and DRX-500 Instruments, respectively. $^{13}$C NMR spectra were recorded on a Bruker Avance DRX-500 instrument at 125.76 MHz. UV-Vis absorption spectra were recorded on an Agilent 8453 diode-array spectrophotometer operating over a range of 190-1100 nm. GC-MS were recorded on an Agilent 6850 Series GC system coupled to an Agilent 5973 mass selective detector run in electron impact mode. Infrared spectra were recorded either on a Mattson Genesis II FT-IR spectrometer or on a PerkinElmer Spectrum 10 spectrometer with an ATR sampling accessory equipped with a diamond anvil. Raman spectra were recorded on a DeltaNu Advantage 532 Raman spectrometer at 532 nm.

Synthesis of PCPDTBT 4,4-Bis(2-ethylhexyl)-2,6-bis(trimethylstannyl)-4H-cyclopenta-[2,1-b;3,4-b']dithiophene was added to a microwave tube along with 4,7-dibromo-2,1,3-benzothiadiazole (1.05:1 equivalent) and 2 mL of chlorobenzene. The tube was stirred for 5 minutes to dissolve the monomers. Pd(PPh$_3$)$_4$ (2.5 mol %) was then added and the tube was sealed with a crimp cap and placed in a microwave reactor where it was heated to 200° C. for 10 minutes. Upon cooling to room temperature a viscous solution of green polymer was observed in the reaction vessel. The polymer was precipitated in methanol and collected by vacuum filtration. The solid was then transferred to a Soxhlet thimble and subjected to extraction with MeOH (3 hrs), hexanes (6 hrs), and finally chloroform (6 hrs). The chloroform extract was evaporated almost to completion and methanol was added to precipitate the polymer, which was filtered and dried under vacuum for 24 hours. $^1$H-NMR is comparable to the literature values.

Synthesis of PCPDTBSe

The synthesis of PCPDTBSe follows the same procedure as PCPDTBT above, except 4,7-dibromo-2,1,3-benzoselenadiazole (1.05:1 equivalent) was used instead of 4,7-dibromo-2,1,3-benzothiadiazole. $^1$H-NMR was comparable to the literature values.

EXAMPLE 2—Synthesis of PCPDTBSe Composite Nanoparticles of Hybrid Architecture 1 mL of low molecular weight PCPDTBSe [2.15 mg/mL in THF] and 1 mL of high molecular weight PCPDTBSe [1 mg/mL in THF] were premixed and injected under continuous horn sonication (10% amplitude, 1 minute) into 8 mL of Pluronic F127 [5 mg/mL in water]. This solution was centrifuged (30 minutes 12,600 Gs) to pellet large nanoparticles; the resulting supernatant was then centrifuged (4 hours 12,600 Gs) to pellet small nanoparticles.

EXAMPLE 3—Synthesis of PCPDTBSe Composite Nanoparticles of Core-Shell Architecture 1 mL of high molecular weight PCPDTBSe [1 mg/mL in THF] followed by 1 mL of low molecular weight PCPDTBSe [2.15 mg/mL in THF] was injected under continuous horn sonication (10% amplitude, 1 minute) into 8 mL of Pluronic F127 [5 mg/mL in water]. This solution was centrifuged (30 minutes 12,600 Gs) to pellet large nanoparticles; the resulting supernatant was then centrifuged (4 hours 12,600 Gs) to pellet small nanoparticles.

EXAMPLE 4—Synthesis of PCPDTBSe-P3HT Composite Nanoparticles of Hybrid Architecture 1 mL of low molecular weight PCPDTBSe [0.5 mg/mL in THF] and 1 mL of high molecular weight PCPDTBSe [0.5 mg/mL in THF] were premixed and injected under continuous horn sonication (45% amplitude, 90 seconds) into 8 mL of phospholipid-poly(ethylene glycol) [molecular weight=3400, 0.25 mg/mL in water]. This solution was centrifuged (30 minutes 12,600 Gs) to pellet large nanoparticles; the resulting supernatant was then centrifuged (4 hours 12,600 Gs) to pellet small nanoparticles.

EXAMPLE 5—Synthesis of PCPDTBSe-P3HT Composite Nanoparticles of Core-Shell Architecture PCPDTBSe is dissolved in 40 mL of toluene is layered on top of 40 mL of water and bath sonicated until all of the toluene was evaporated forcing PCPDTBSe into the water (generating nanoPCPDTBSe). This solution was centrifuged (30 minutes 12,600 Gs) to pellet large nanoparticles; the resulting supernatant was then centrifuged (4 hours 12,600 Gs) to pellet small nanoparticles (approximately 60 nm in diameter). 2 mL of P3HT [0.25, 0.5, 0.75, 1, 1.5, 2, 3, or 4 mg/mL in THF] is rapidly injected under continuous horn sonication (15% amplitude, 1 minute) into 8 mL of the small nanoPCPDTBSe [0.1 mg/mL in water]. This solution was centrifuged (30 minutes 12,600 Gs) to pellet large nanoparticles; the resulting supernatant was then centrifuged (4 hours 12,600 Gs) to pellet small nanoparticles.

EXAMPLE 6—Cytotoxicity Evaluation of Composite Nanoparticles

MCF10A and MDA-MB-231 cells were plated in 96 well plates (5,000 cells/well). The next day, composite nanoparticle solutions were added to wells [0, 5, 10, 15, 20, 30, 40, 50, 100 μg/mL in appropriate media] and allowed to incubate 24 hours. Composite nanoparticle solutions were removed, wells washed once with PBS, MTS solution added (20 μL 96AQ and 100 μL media per well) and allowed to incubate 1-4 hours. MTS solutions moved to a new plate, absorption read at 492 nm, and values normalized to 0 μg/mL control. Results of the cytotoxicity study are provided in FIG. 12.

EXAMPLE 7—Thermal Ablation of Cancer Cells

MCF10A and MDA-MB-231 cells were plated in 96 well plates (5,000 cells/well). The next day, composite nanoparticle solutions were added to wells [0, 5, 10, 15, 20, 30, 40, 50, 100 μg/mL in appropriate media] and allowed to incubate 30 minutes (to warm to 37° C.). Wells exposed to 800 nm light (3 watts, continuous wavelength, 1 minute), then nanoparticle solutions were removed, wells washed once with PBS, MTS solution added (20 μL, 96AQ and 100 μL media per well) and allowed to incubate 1-4 hours. MTS solutions moved to a new plate, absorption read at 492 nm, and values normalized to 0 μg/mL control. Results of the ablation studies are provided in FIG. 13.

EXAMPLE 8—Conjugated Polymer Synthesis

Synthesis of poly[4,4-bis(2-ethylhexyl)cyclopenta[2,1-b;3,4-b]dithiophene-2,6-diyl-alt-2,5-Diethylhexyl-3,6-bis(thiophen-2-yl)pyrrolo[3,4-c]-pyrrole-1,4-dione]

4,4-Bis(2-ethylhexyl)-2,6-bis(trimethyl-stan-nyl)-4H-cyclopenta-[2,1-b;3,4-b']dithiophene (728.3 mg) was added to a 250 mL 3 neck round bottom flask with 2,5-diethylhexyl-3,6-bis(5-bromothiophen-2-yl)pyrrolo[3,4-c]-pyrrole-1,4-dione (682.5 mg) and 40 mL of toluene. The solution was stirred and degassed for 15 minutes. Pd(PPh$_3$)$_4$ (100 mg) was added and the solution was further degassed for 15 min. The solution was heated to 120° C. for 24 hours. Upon cooling to room temperature a viscous solution of blue/green polymer was observed in the reaction vessel. The polymer was precipitated in methanol and collected by vacuum filtration. The solid was then transferred to a Soxhlet thimble and subjected to extraction with MeOH (3 hrs), hexanes (6 hrs), and finally chloroform (6 hrs). The chloroform extract was evaporated almost to completion and methanol was added to precipitate the polymer, which was filtered and dried under vacuum for 24 hours (Yield 82 mg).

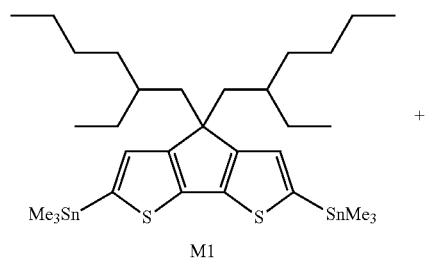

M1

+

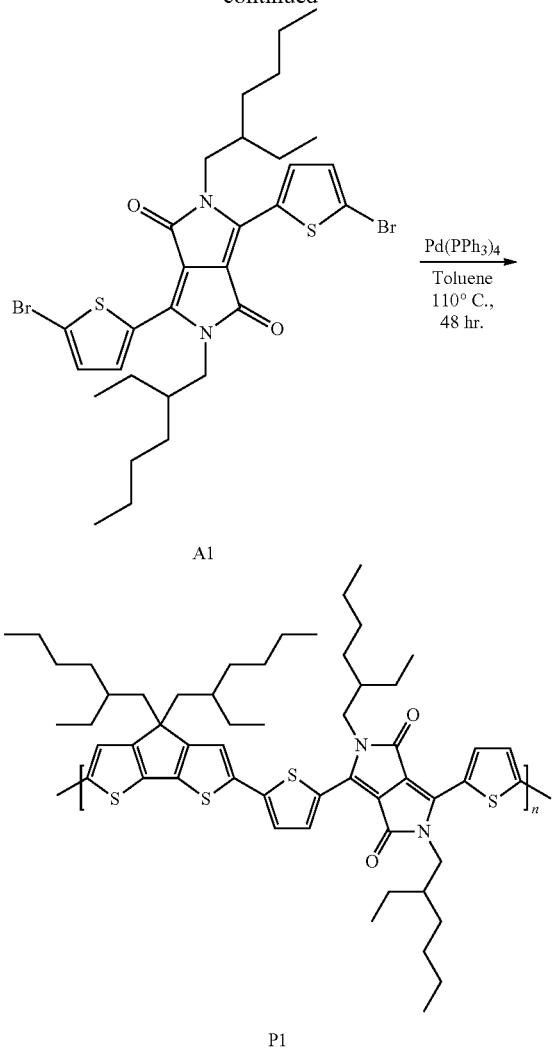

A1

P1

EXAMPLE 9—Synthesis of Folic Acid (FA) Modified Conjugated Polymer

Synthesis of FA-functionalized poly[4,4-bis(2-ethylhexyl)cyclopenta[2,1-b;3,4-b']dithiophene-2,6-diyl-alt-2,5-Ditetraethyleneglycol-3,6-bis(thiophen-2-yl)pyrrolo[3,4-c]-pyrrole-1,4-dione] (P3)

4,4-Bis(2-ethylhexyl)-2,6-bis(trimethyl-stannyl)-4H-cyclopenta-[2,1-b;3,4-b']dithiophene was added to a 250 mL 3 neck round bottom flask with 2,5-diethylhexyl-3,6-bis(5-bromothiophen-2-yl)pyrrolo[3,4-c]-pyrrole-1,4-dione and 40 mL of toluene. The solution was stirred and degassed for 15 minutes. Pd(PPh$_3$)$_4$ was added and the solution was further degassed for 15 min. The solution was heated to 120° C. for 24 hours. Upon cooling to room temperature a viscous solution of blue/green polymer was observed in the reaction vessel.

The polymer was precipitated in methanol and collected by vacuum filtration. The solid was then transferred to a Soxhlet thimble and subjected to extraction with MeOH (3 hrs), hexanes (6 hrs), and finally chloroform (6 hrs). The chloroform extract was evaporated almost to completion and methanol was added to precipitate the polymer, which was filtered and dried under vacuum for 24 hours.

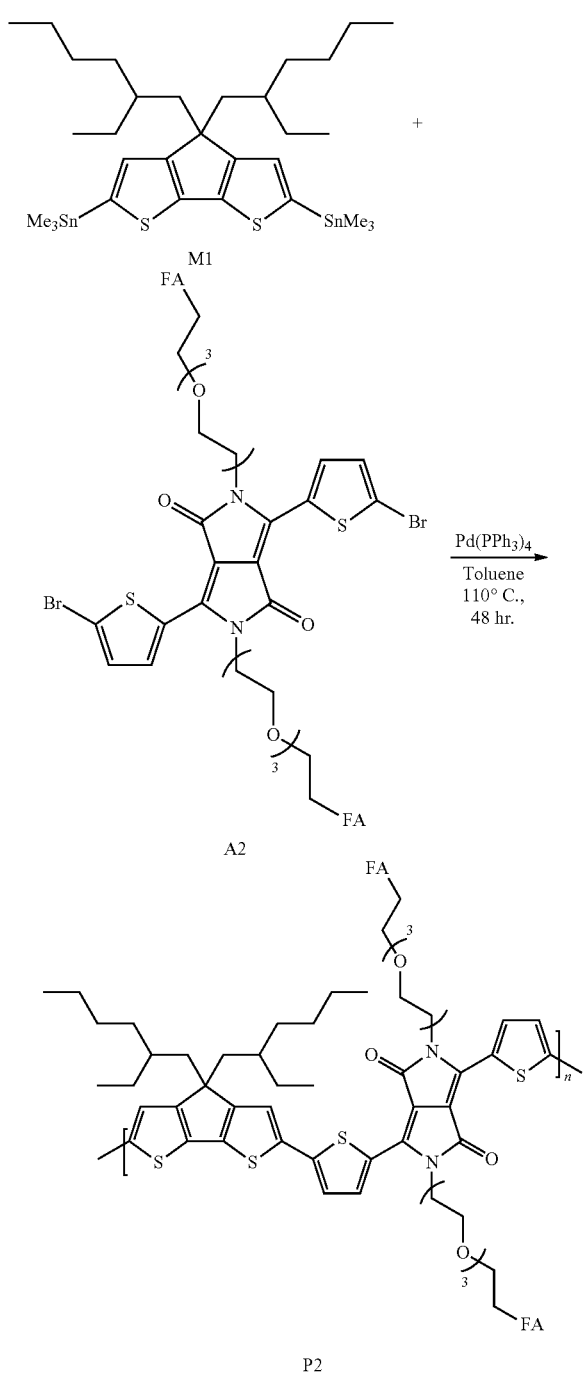

EXAMPLE 10—Elastomer Comprising Composite Nanoparticles

Equimolar ratios of 1,8-octanediol and citric acid were reacted in a round bottom flask under continuous stirring and nitrogen purge. Initially, the reagents were melted together at 165° C. and then the reaction temperature was reduced to 140° C. and the monomers stirred for one hour under continuous nitrogen purge. The pre-polymer was precipitated in water to remove unreacted citric acid and the water removed by evaporation. POC solidifies at room temperature and can be made into a viscous solution by heating it briefly.

The POC was heated in a container at 120 C permitting the POC to be poured into a 25 ml beaker (3.33 g) 0.001% composite nanoparticles (PCPDTBSe) v/w was determined. 111 µL of the composite nanoparticles in water was added to the warm POC. The resulting elastomer-nanoparticle composition was mixed thoroughly by hand and then sonicated twice for 30 seconds each. The mixture was heated to 80° C. and poured onto a PTFE sheet. The PTFE sheet was placed in a vacuum oven at 80° C. and left overnight. The composition was subsequently checked hourly until a suitable glass transition temperature was reached.

EXAMPLE 11—Cytotoxicity and Ablation Study of Composite Nanoparticles

Figure 16:
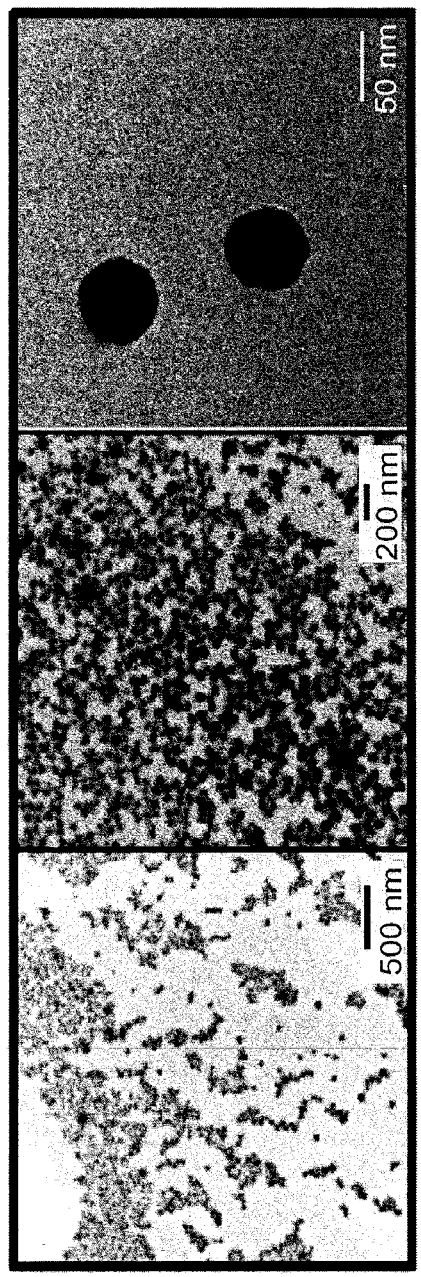
FIG. 16 provides TEM images of composite nanoparticles at various magnifications according to one embodiment described herein.
Figure 17:
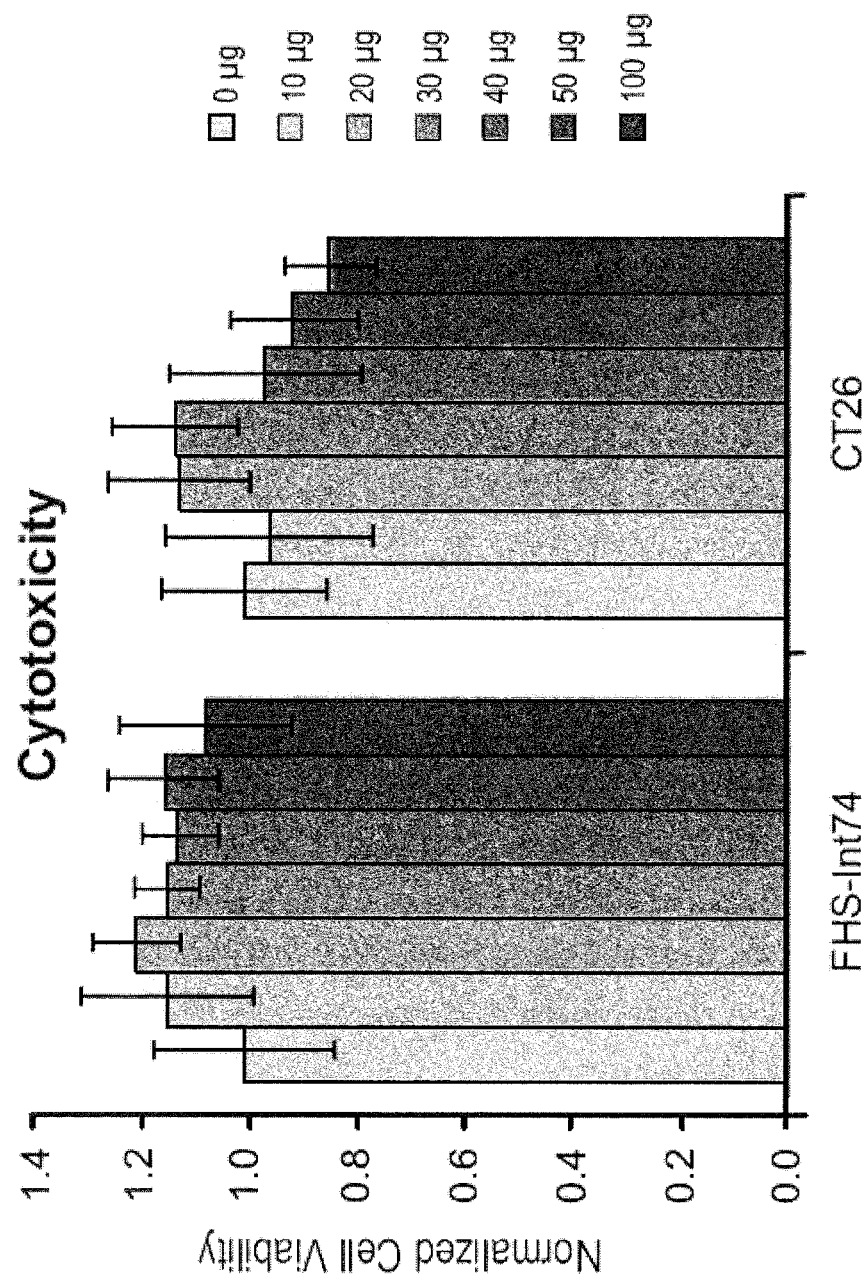
FIG. 17 illustrates results of a cytotoxicity study employing composite nanoparticles according to one embodiment described herein.
Figure 18:
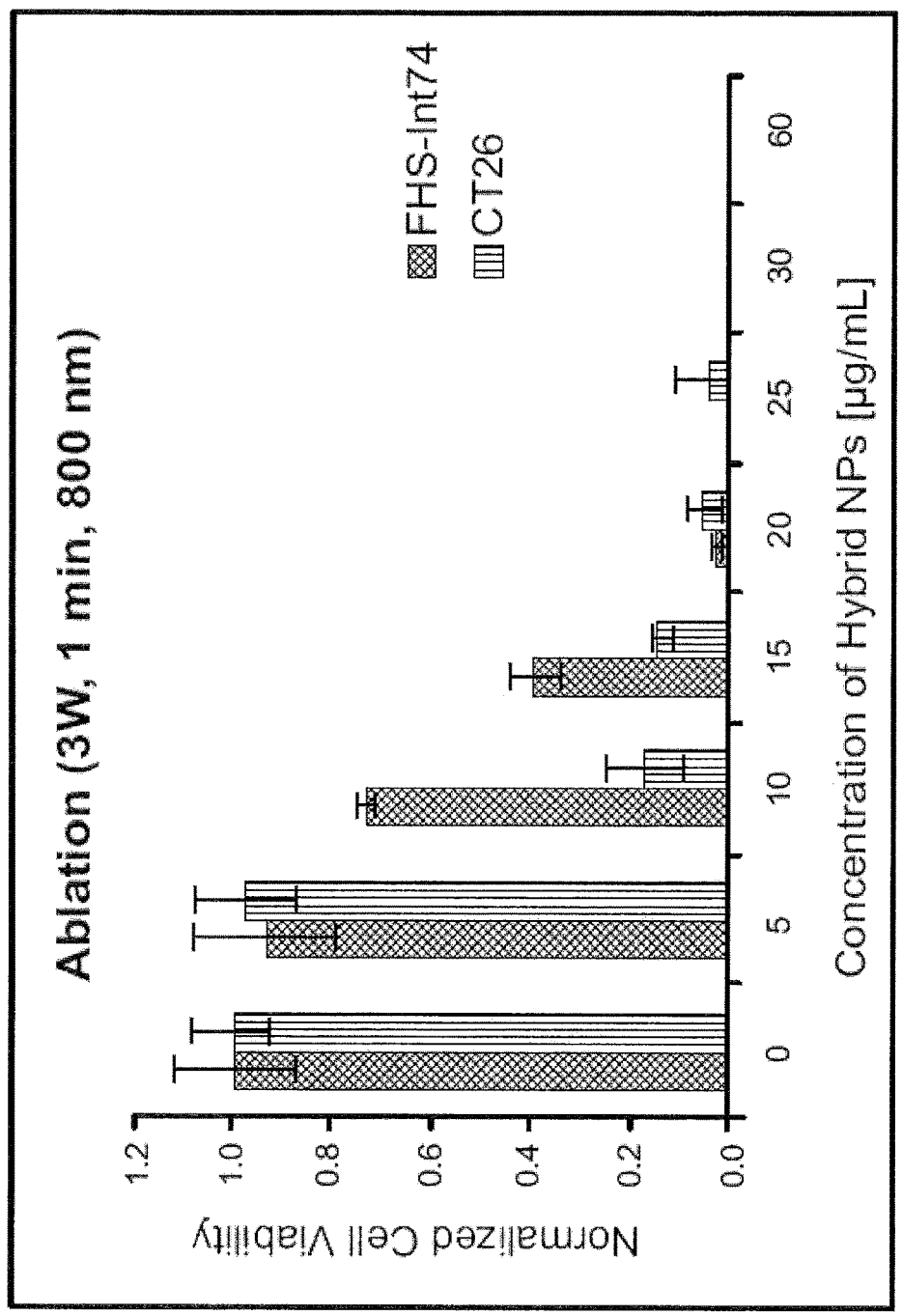
FIG. 18 illustrates results of a cellular ablation study employing composite nanoparticles according to one embodiment described herein.

PCPDTBSe-P3HT composite nanoparticles having hybrid architecture were fabricated in accordance with the Example 4 and exhibited an average diameter of 130 nm. TEM images of the composite nanoparticles at various magnifications are provided in FIG. 16. FHS-Int74 and CT26 cells were placed in 96 well plates (5,000 cells/well). The following day PCPDTBSe-P3HT composite nanoparticle solutions were added to the wells [0, 10, 20, 30, 40, 50 and 100 µg/mL in appropriate media] and allowed to incubate for 24 hours. Composite nanoparticle solutions were removed, wells washed once with PBS, MTS solution added (20 µL 96 AQ and 100 µL, media per well) and allowed to incubate 1-4 hours. MTS solutions were moved to a new place, absorption read at 492 nm and values normalized to 0 µg/mL control. The composite nanoparticles did not exhibit appreciable cytotoxicity as illustrated in FIG. 17. Thermal ablation of the FHS-Int74 and CT26 cells was then conducted in accordance with the procedure of Example 7. As illustrated in FIG. 18, negligible cell viability was measured at composite nanoparticle concentrations greater than 20 µg/mL.

EXAMPLE 12—Synthesis of Hybrid Composite Nanoparticles Employing PFBTDBT10

Figure 19:
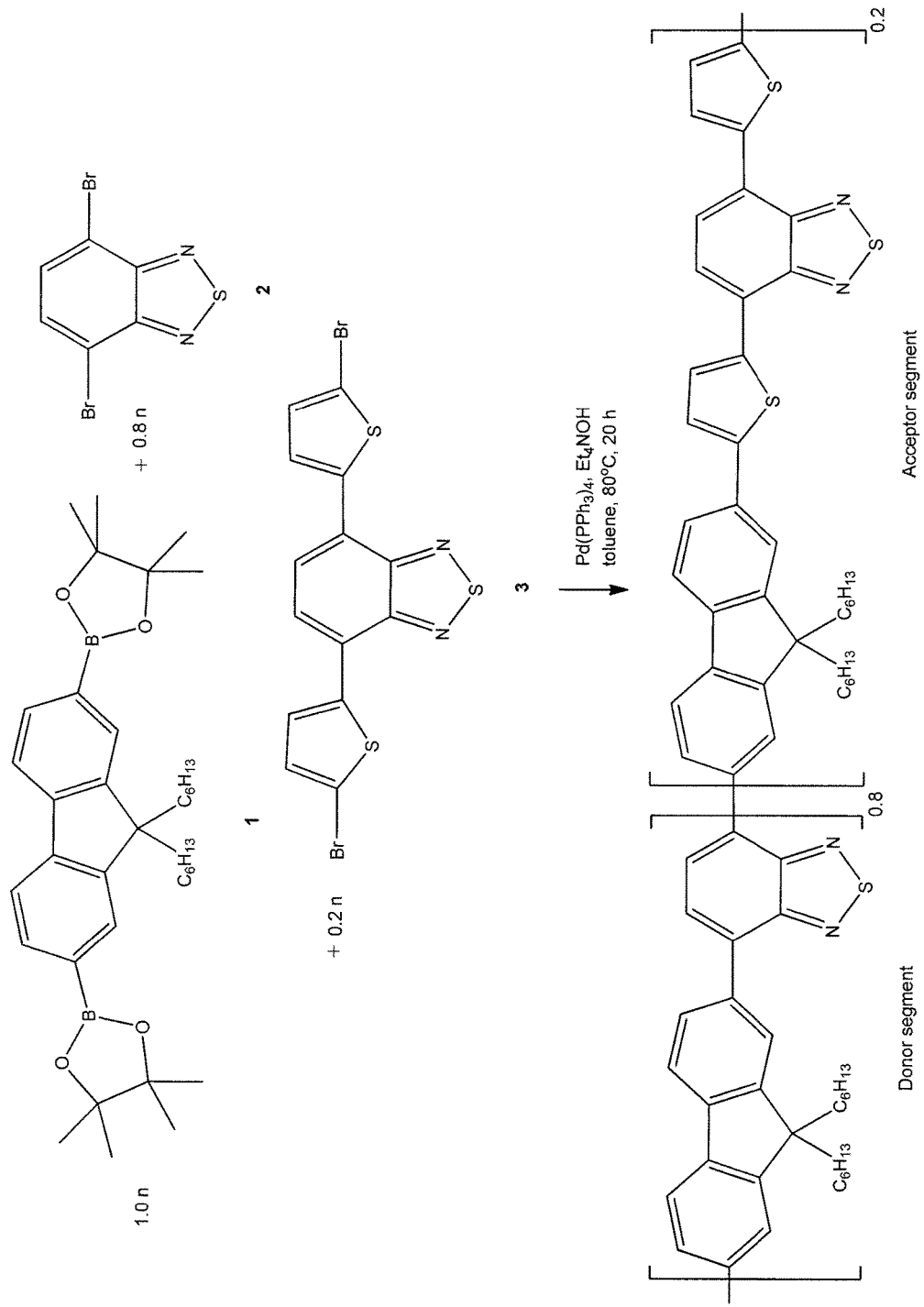
FIG. 19 provides a synthetic pathway for a polymeric or oligomeric photoluminescent component of composite nanoparticles according to some embodiments described herein.

Photoluminescent component of poly[9,9-dihexylfluorene)-co-2,1,3-benzothiadiazole-co-4,7-di(thiophen-2-yl)-2,1,3-benzothiadiazole) (PFBTDBT10) was synthesized according the reaction scheme provided in FIG. 19 and exhibited a molecular weight of 40,000-45,000 g/mol. The PFBTDBT10 was mixed with photo-thermal component of PCPDTBSe in THF and injected into 8 mL of [0.25 mg/mL] of DSPE-PEG$_{3400}$-COOH under 1 minute of 20% horn sonication to provide PFBTDBT10-PCPDTBSe hybrid composite nanoparticles. Two samples of hybrid composite nanoparticles were synthesized according to this example as provided in Table VII.

TABLE VII

| PFBTDBT10-PCPDTBSe hybrid composite nanoparticles | | | |
|---|---|---|---|
| Sample | PFBTDBT10 added to THF | PCPDTBSe added to THF | Ratio in Composite Nanoparticle |
| DBT10-BSE #4 | 1.9 mg | 0.10 mg | 4:1 |
| DBT10-BSE #12 | 1.95 mg | 0.05 mg | 8:1 |

Figure 20:
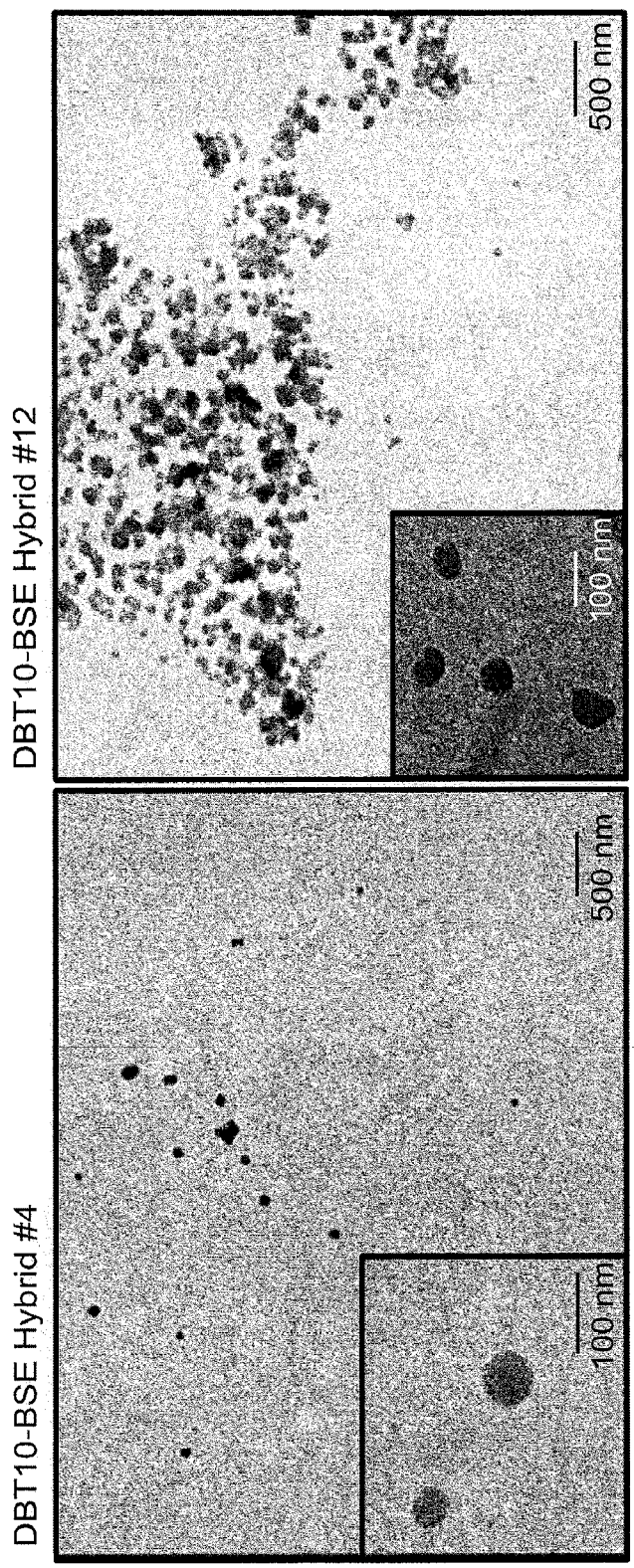
FIG. 20 provides TEM images of composite nanoparticle compositions according to some embodiments described herein.
Figure 21:
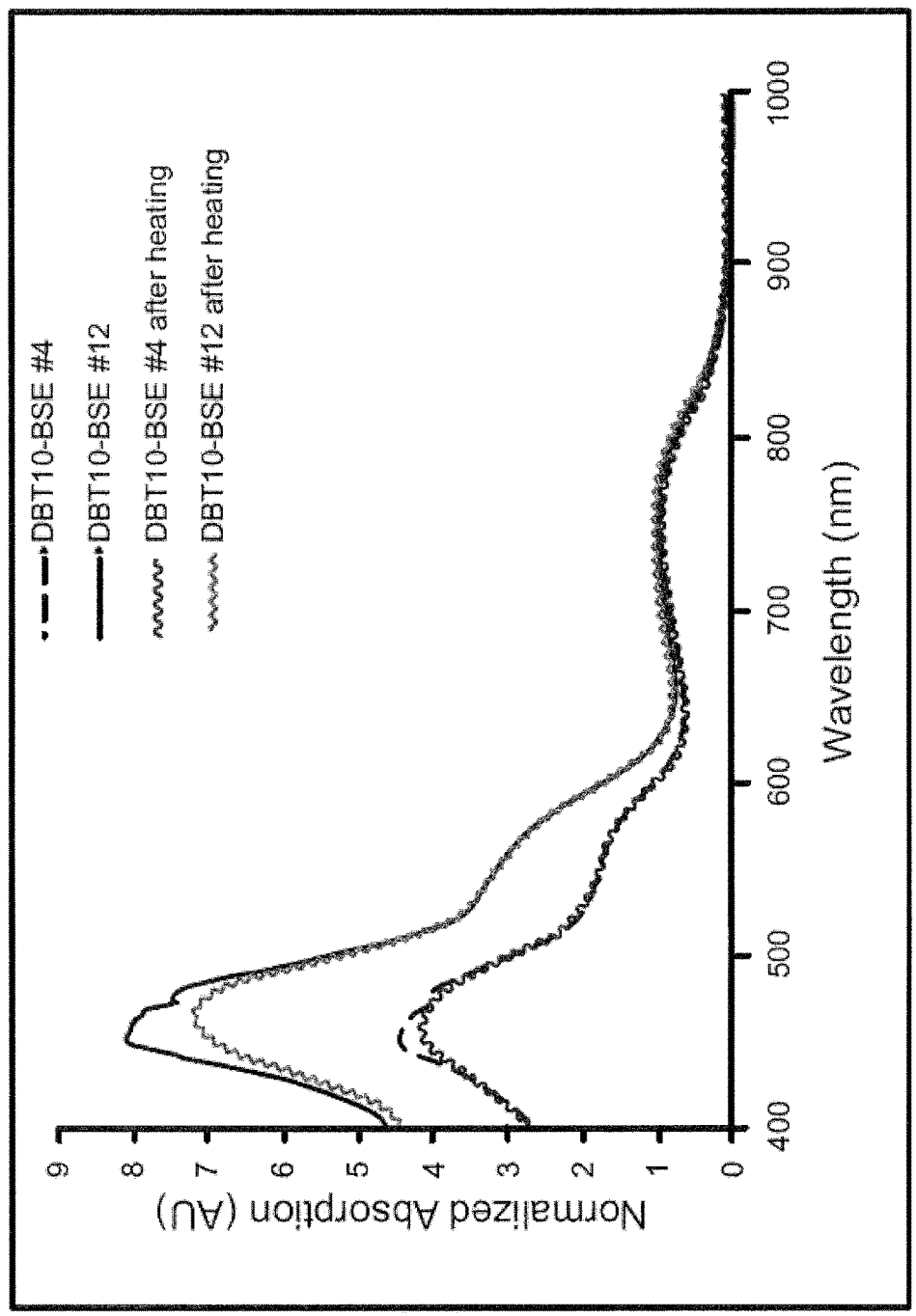
FIG. 21 illustrates absorption spectra for composite nanoparticles pre- and post-heating according to some embodiments described herein.
Figure 22:
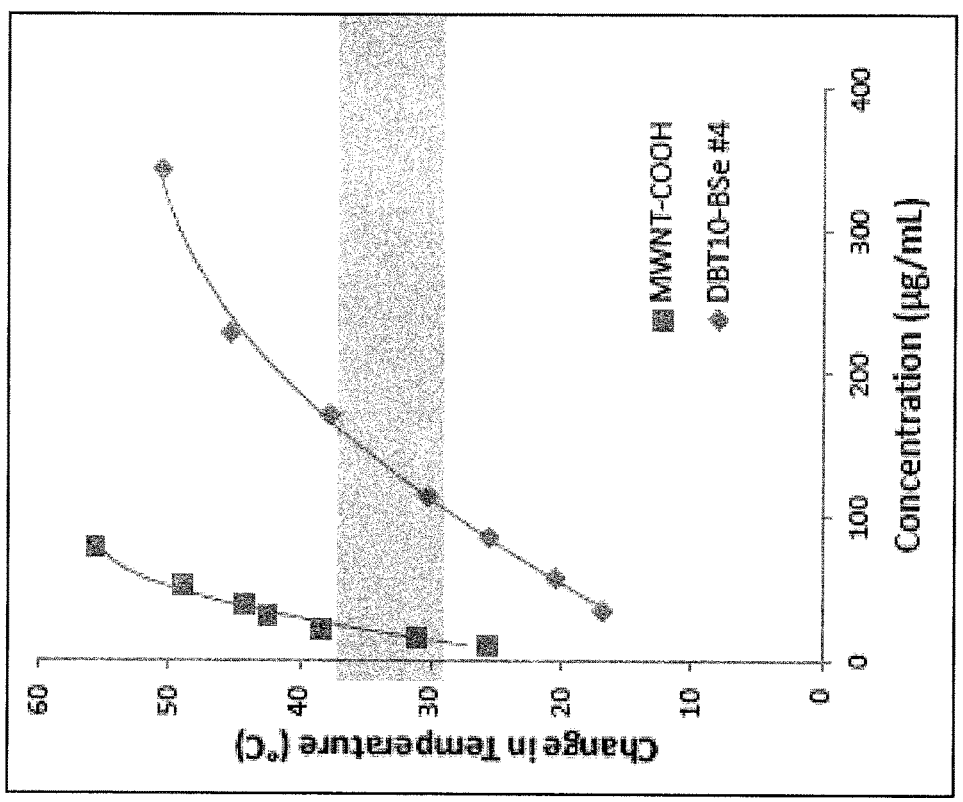
FIG. 22 illustrates thermal response of a composite nanoparticle composition described herein relative to multi-walled carbon nanotubes.

The PFBTDBT10-PCPDTBSe hybrid composite nanoparticles exhibited a substantially uniform distribution and spherical morphology of diameter 50-70 nm as illustrated in the TEM images of FIG. 20. Heating of the PFBTDBT10-PCPDTBSe hybrid composite nanoparticles did not affect absorption of electromagnetic radiation as provided in FIG. 21. Moreover, heating properties of DBT10-BSe #4 composite nanoparticles were compared with MWNT-COOH nanoparticles under irradiation conditions of 1 minute, 3 W, CW, 800 nm light. Results of the heating comparison are provided in FIG. 22.

EXAMPLE 13—Cytotoxicity Study of PFBTDBT10-PCPDTBSe Hybrid Composite Nanoparticles PFBTDBT10-PCPDTBSe hybrid composite nanoparticles were prepared in accordance with Example 12. Tib80, 4T1 and EO771 cells were plated in 96 well plates (10,000 cells/well) in 200 µL of media. 24 hours later 200 µL of PFBTDBT10-PCPDTBSe hybrid composite nanoparticle solutions were added to the wells [0, 25, 50, 75, 100, 125, 150 µg/mL in appropriate media] and allowed to incubate. After 24 hours, the nanoparticle solutions were removed and the cells washed two times with PBS, MTS solution added (20 µL 96 AQ and 100 µL media per well) and allowed to incubate for 2-3 hours at 37° C. MTS solutions moved to a new plate and absorption read at 490 nm, and values normalized to 0 µg/mL control. Results provided in FIG. 23 indicated no cytotoxicity across all nanoparticle concentrations.

EXAMPLE 14—Ablation Study of PFBTDBT10-PCPDTBSe Hybrid Composite Nanoparticles

PFBTDBT10-PCPDTBSe hybrid composite nanoparticles were prepared in accordance with Example 12. Tib80, 4T1 and EO771 cells were plated in 96 well plates (10,000 cells/well) in 200 µL of media. 24 hours later 200 µL of PFBTDBT10-PCPDTBSe hybrid composite nanoparticle solutions were added to the wells [0, 10, 20, 30, 40, 50, 60, 70, 80, 90, 100 µg/mL in appropriate media] and the cells exposed to NIR light (3 W, CW, 1 minute, 1 cm spot size). The nanoparticle solutions were removed, wells washed twice PBS, MTS solution added (20 µL 96AQ and 100 µL of media per well) and allowed to incubate 24 hours. MTS solutions were moved to a new plate, absorption read at 492 nm and values normalized to 0 µg/mL control.

Figure 24:
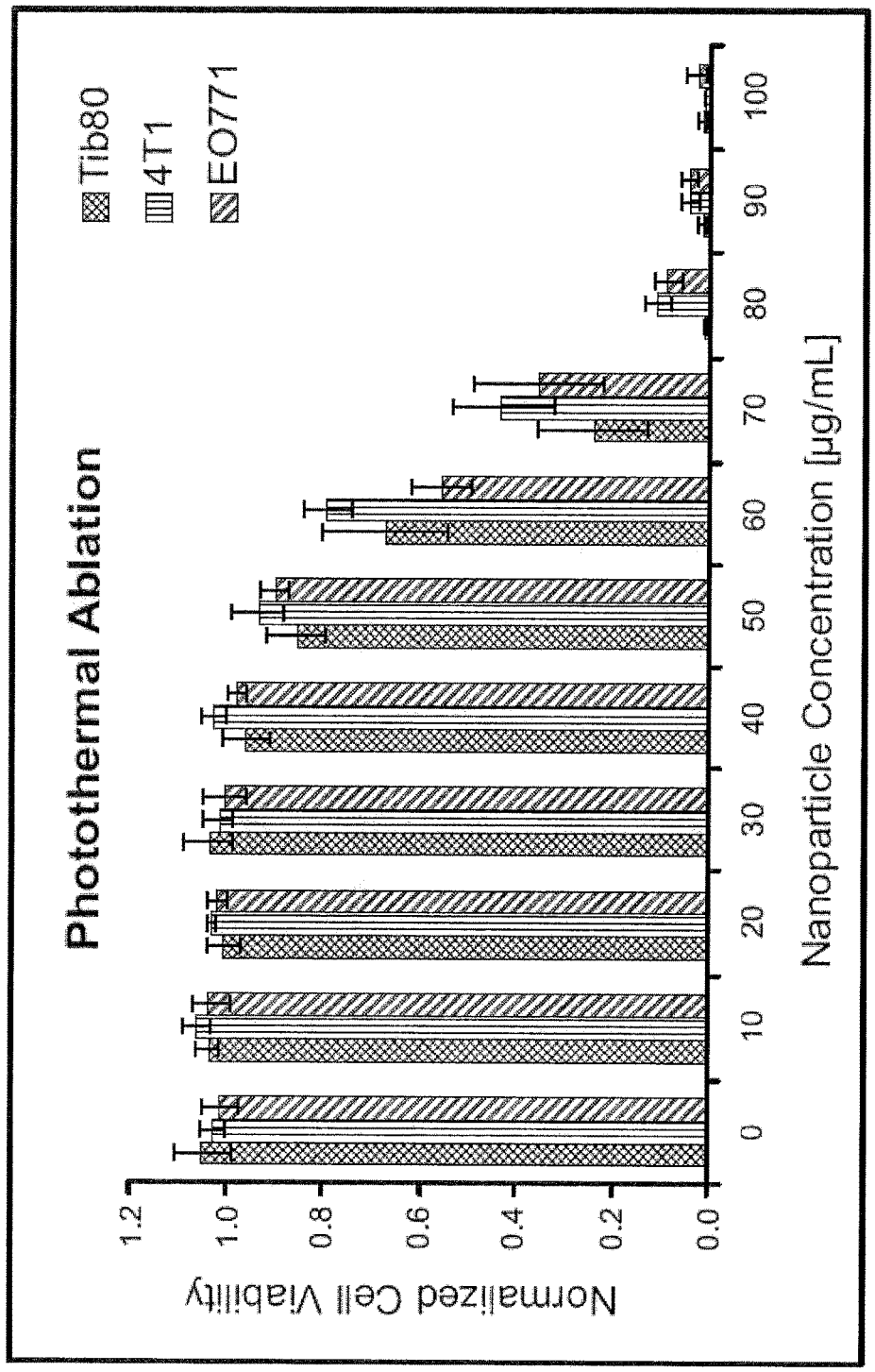
FIG. 24 illustrates results of a cellular ablation study employing composite nanoparticles according to one embodiment described herein.

Results of the ablation study are illustrated in FIG. 24.

Figure 25:
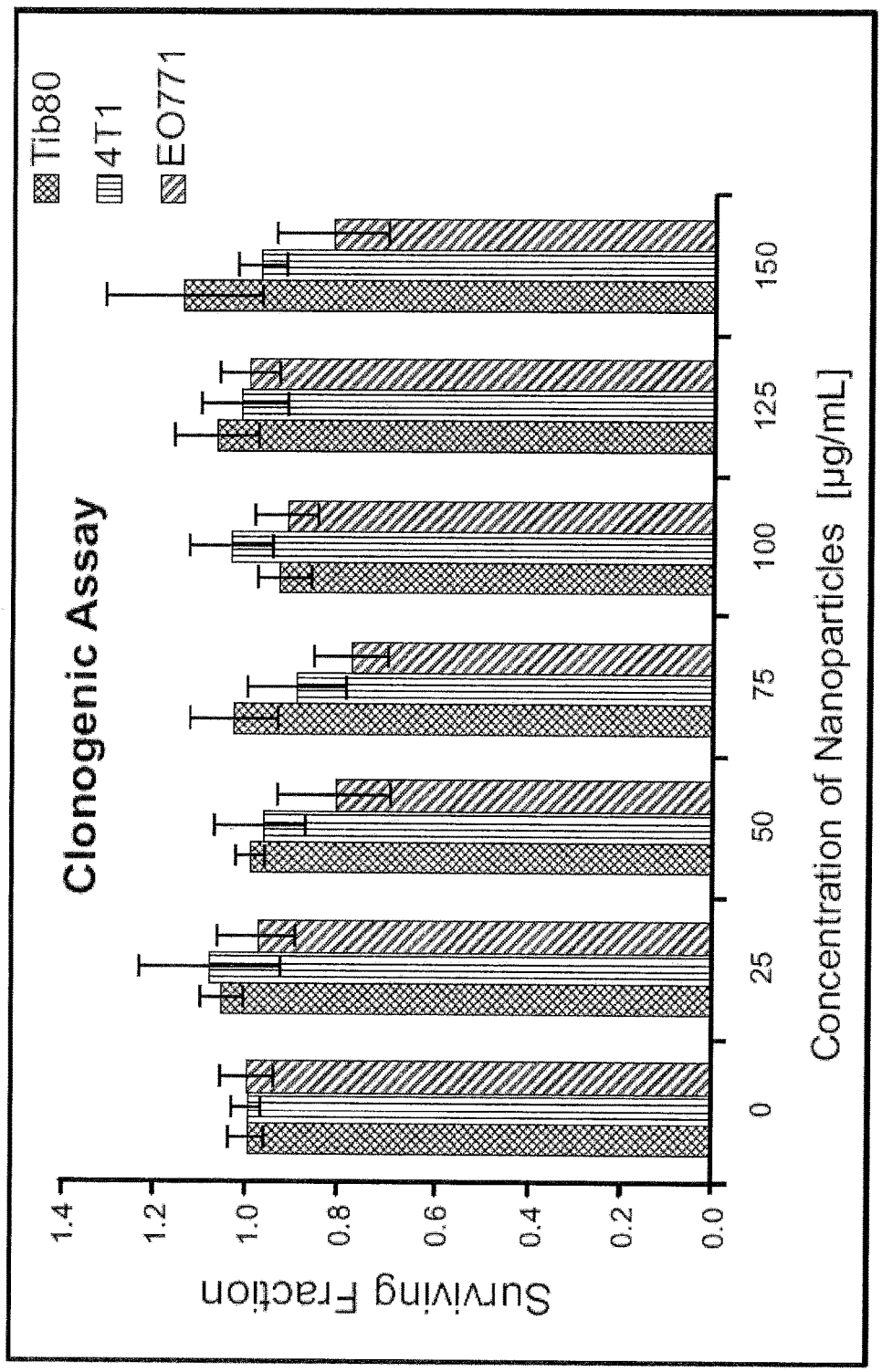
FIG. 25 illustrates results of a clonogenic study employing composite nanoparticles according to one embodiment described herein.

EXAMPLE 15—Clonogenic Study of PFBTDBT10-PCPDTBSe Hybrid Composite Nanoparticles PFBTDBT10-PCPDTBSe hybrid composite nanoparticles were prepared in accordance with Example 12. Tib80, 4T1 and EO771 cells were plated in 12 well plates (100-150 cells/well) in 1000 µL of media. 24 hours later PFBTDBT10-PCPDTBSe hybrid composite nanoparticles solutions were added to the wells [0, 25, 50, 75, 100, 125, 150 µg/mL in appropriate media]. 24 hours later, the composite nanoparticle solutions were removed, the cells washed with PBS and media added. Media was changed every 2 days. 7 days after plating, the cells were fixed and stained with crystal violet. Colonies with 50+ cells were counted and normalized to 0 µg/mL control. According to the results provided in FIG. 25, the PFBTDBT10-PCPDTBSe hybrid composite nanoparticles did not appeal to cause any clonogenic effects.

Heating Data for Composite Materials:

POC was fabricated without any composite nanoparticles for a comparison of heating properties with the POC-composite nanoparticle composition described above. A small sample of each material was placed in 2 ml of saline for evaluation of photo-thermal response. The average sample size was 0.27 g. 800 nm light at a frequency of 20,000 Hz was applied to samples at a power of 2.5 W for 300 s. For POC alone without nanoparticles, the average temperature change of the water solution was 8.0° C. For POC with 0.001% composite nanoparticles (PCPDTBSe), the average temperature change of the water was 29.7° C.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A composite nanoparticle comprising:
photoluminescent polymeric component; and
a photo-thermal polymeric component,
wherein the photo-thermal component comprises poly[4,4-bis(2-ethylhexvl)cyclopenta[2,1-b:3,4-b']dithiophene-2,6-diyl-alt-2,5-diethylhexyl-3,6-bis(thiophen-2-yl)pyrrolor[3,4-c]-pyrrole-1,4-dione].

2. The composite nanoparticle of claim 1, wherein the photoluminescent polymeric component comprises a polymeric species having a molecular weight lower than a polymeric species of the photo-thermal polymeric component.

3. The composite nanoparticle of claim 1, wherein the photoluminescent polymeric component comprises a polymeric species having a wider bandgap than a polymeric species of the photo-thermal polymeric component.

4. The composite nanoparticle of claim 2, wherein the polymeric species of the photoluminescent polymeric component is the same polymeric species as the photo-thermal polymeric component.

5. The composite nanoparticle of claim 1, wherein the photoluminescent polymeric component and the photo-thermal polymeric component are present throughout the nanoparticle.

6. The composite nanoparticle of claim 1, wherein the photoluminescent polymeric component and the photo-thermal polymeric component are localized to different regions of the composite nanoparticle.

7. The composite nanoparticle of claim 6, wherein the photo-thermal polymeric component is localized to the core of the composite nanoparticle and the photoluminescent polymeric component is localized to surfaces of the composite nanoparticle.

8. The composite nanoparticle of claim 7, wherein the photoluminescent polymeric component forms a shell over the photo-thermal polymeric component.

9. The composite nanoparticle of claim 1, wherein a ratio of the photo-thermal polymeric component to the photoluminescent polymeric component ranges from 1:10 to 10:1.

10. The composite nanoparticle of claim 1, wherein the photoluminescent polymeric component comprises one or more species of conjugated polymer operable to photoluminesce in the visible or infrared region of the electromagnetic spectrum.

11. The composite nanoparticle of claim 10, Wherein the photo-thermal polymeric component comprises one or more species of conjugated polymer operable to generate heat when irradiated with radiation of wavelength 700 nm to 1000 nm.

12. The composite nanoparticle of claim 1 having a size of 1 nm to 500 nm.

13. The composite nanoparticle of claim 11, wherein the photoluminescent polymeric component comprises polymer species having a donor-acceptor architecture comprising a donor monomeric species (D) and an acceptor monomeric species (A).

14. The composite nanoparticle of claim 13, wherein the photo-thermal polymeric component comprises polymer species having a donor-acceptor architecture comprising a donor monomeric species (D) and an acceptor monomeric species (A).

15. The composite nanoparticle of claim 14, wherein the donor-acceptor architecture is of the formula

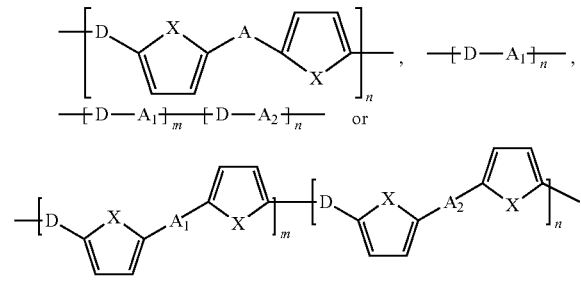

wherein D is a donor monomeric species, A and $A_1$ are an acceptor monomeric species, m and n range from 1 to 100 and each X is independently O, N, S, Se or Te.

16. The composite nanoparticle of claim 15, wherein the donor-acceptor architecture is of the formula

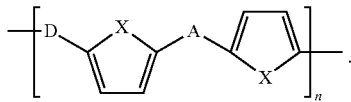

17. The composite nanoparticle of claim 1, wherein the photothermal polymeric component comprises poly [4,4-bis(2-ethylhexyl)-cyclopenta[2,1-b;3,4-b ']dithiophene-2,6-diylalt-2,1,3-benzoselenadiazole-4,7-diyl], and the photoluminescent component comprises poly[(9,9-dihexylfluorene)-co-2,1,3-benzothiadiazole-co-4,7-di(thiophen-2-yl)-,1,3-benzothiadiazole.

18. The composite nanoparticle of claim 17, wherein the poly [4,4-bis(2-ethylhexyl)-cyclopenta[2,1-b ;3,4 -b']dithiophene-2,6-diylalt-2,1,3-benzoselenadiazole-4,7-diyl]has a molecular weight ranging from 20,000 to 35,000 Da.

19. The composite nanoparticle of claim 1, wherein the polymeric photoluminescent component is substituted with an oligomeric photoluminescent component.

20. The composite nanoparticle of claim 19, wherein the oligomeric photoluminescent component comprises oligomeric [(9,9-dihexylfluorene)-co-2,1,3-benzothiadiazole-co-4,7-di(thiophen-2-yl)-2,1,3-benzothiadiazole.

21. The composite nanoparticle of claim 1 further comprising one or more active agents associated with the photoluminescent polymeric component, the photo-thermal polymeric component or both.

22. The composite nanoparticle of claim 21, wherein the one or more active agents comprise an antibody, a chemokines receptor, a targeting ligand, protein, amino acid or nucleic acid.

23. A composition comprising:
an aqueous or aqueous-based medium; and
composite nanoparticles disposed in the aqueous or aqueous-based medium, the nanoparticles comprising a photoluminescent polymeric component and a photo-thermal polymeric component,
wherein the photo-thermal component comprises poly[4,4-bis(2-ethylhexyl)cyclopenta[2,1-b;3,4-b']dithiophene-2,6-diyl-alt-2,5-diethylhexyl-3,6-bis(thiophen-2-yl)pyrrolo[3,4-c]-pyrrole-1,4-dione].

24. The composition of claim 23, wherein the nanoparticles are present in the aqueous or aqueous-based medium an amount of 1 fg/mL to greater than 1 mg/mL.

25. The composition of claim 23, wherein the nanoparticles are present in the aqueous or aqueous-based medium an amount of 5 µg/mL to 100 µg/mL.

26. The composition of claim 23, wherein the photoluminescent polymeric component comprises a polymeric species having a molecular weight lower than a polymeric species of the photo-thermal polymeric component.

27. The composition of claim 23, wherein the photoluminescent polymeric component and the photo-thermal polymeric component are present throughout the nanoparticle.

28. The composition of claim 23, wherein the photoluminescent polymeric component and the photo-thermal polymeric component are localized to different regions of the composite nanoparticle.

29. The composition of claim 28, wherein the photo-thermal polymeric component is localized to the core of the composite nanoparticle and the photoluminescent polymeric component is localized to surfaces of the composite nanoparticle.

30. The composition of claim 23, wherein the ratio of photo-thermal polymeric component to the photoluminescent polymeric component ranges from 1:10 to 10:1.

31. The composition of claim 23, wherein the photoluminescent polymeric component comprises polymer species having a donor-acceptor architecture comprising a donor monomeric species (D) and an acceptor monomeric species (A).

32. The composition of claim 31, wherein the photo-thermal polymeric component comprises polymer species having a donor-acceptor architecture comprising a donor monomeric species (D) and an acceptor monomeric species (A).

33. The composition of claim 32, wherein the donor-acceptor architecture is of the formula

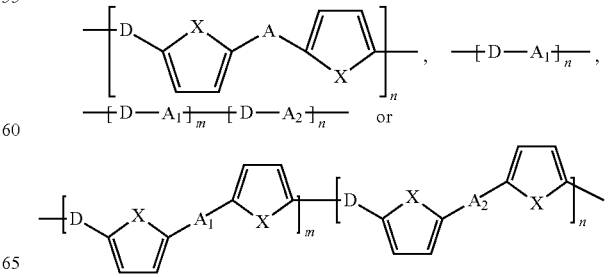

wherein D is a donor monomeric species, A and $A_1$ are an acceptor monomeric species, m and n range from 1 to 100 and each X is independently O, N, S, Se or Te.

34. The composition of claim 23, wherein the photothermal polymeric component comprises poly[4,4-bis(2-ethylhexyl)-cyclopenta[2,1-b;3,4-b']dithiophene-2,6-diyl-alt-2,1,3-benzoselenadiazole-4,7-divyl]and the photoluminescent component comprises poly [(9,9-dihexylfluorene)-co-2,1,3-benzothiadiazole-co-4,7-di(thiophen-2-yl)-2,1,3-benzothiadiazole.

35. The composition of claim 34, wherein the poly[4,4-bis(2-ethylhexyl)-cyclopenta[2,1-b;3,4-b']dithiophene-2,6-diylalt-2,1,3-benzoselenadiazole-4,7-diyl]has a molecular weight ranging from 20,000 to 35.000 Da.

36. The composition of claim 25, wherein the composite nanoparticles are operable to heat the aqueous or aqueous-based medium to a temperature in excess of 35° C. when irradiated with a laser of wavelength 700 nm to 1000 nm.

37. The composition of claim 36, wherein the composite nanoparticles are operable to repeatedly heat the aqueous or aqueous-based medium to a temperature in excess of 35° C. when cyclically irradiated with a laser of wavelength 700 nm to 1000 nm after cooling to room temperature.

38. The composition of claim 36, wherein heating by the composite nanoparticles reduces photoluminescence of the composite nanoparticles by less than 10%.

* * * * *